(12) United States Patent
Raines et al.

(10) Patent No.: US 9,988,434 B2
(45) Date of Patent: Jun. 5, 2018

(54) OPTIMAL INTERSTRAND BRIDGE FOR COLLAGEN MIMICS

(71) Applicant: Wisconsin Alumni Research Foundation, Madison, WI (US)

(72) Inventors: Ronald T. Raines, Madison, WI (US); Ismet C. Tanrikulu, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 15 days.

(21) Appl. No.: 14/852,011

(22) Filed: Sep. 11, 2015

(65) Prior Publication Data

US 2016/0075764 A1 Mar. 17, 2016

Related U.S. Application Data

(60) Provisional application No. 62/049,550, filed on Sep. 12, 2014.

(51) Int. Cl.
*C07K 14/78* (2006.01)
*A61L 26/00* (2006.01)

(52) U.S. Cl.
CPC .......... *C07K 14/78* (2013.01); *A61L 26/0033* (2013.01); *A61L 26/0066* (2013.01)

(58) Field of Classification Search
CPC .. A61L 26/0033; A61L 26/0066; C07K 14/78
See application file for complete search history.

(56) References Cited

U.S. PATENT DOCUMENTS

2007/0275897 A1 11/2007 Raines

FOREIGN PATENT DOCUMENTS

| EP | 0410537 A1 * | 1/1991 | ............ C07K 5/126 |
| WO | WO 9300108 A1 * | 1/1993 | ........... C07K 5/0227 |
| WO | WO 9812219 A1 * | 3/1998 | ............... C07K 7/06 |

OTHER PUBLICATIONS

Hubmacher et al., Biochemistry, vol. 50:5322-5332 (May 11, 2011).*

(Continued)

*Primary Examiner* — Randall L Beane
(74) *Attorney, Agent, or Firm* — Quarles & Brady LLP

(57) ABSTRACT

Novel collagen-mimetic peptides are disclosed comprising the formula (Xaa-Yaa-Gly)$_n$, where the amino acid at one of the Xaa positions is substituted with a homocysteine residue. Also disclosed are multi-stranded novel collagen-mimetic peptides comprising a first strand as described above that is covalently bonded with a disulfide bridge to a second strand comprising the formula (Xaa-Yaa-Gly)$_m$, where the amino acid at one of the Yaa positions is substituted with a cysteine residue. Disulfide formation between the terminal thiol sulfur of the homocysteine residue of the first strand and the terminal thiol sulfur of the cysteine residue of the second strand reveals unstrained bridges that enhance the structure and substantially improve the stability of collagen triple helices as compared to other possible disulfide or thioether bridges. Thus, the disclosed collagen mimetic peptides have improved stability, and can be used to produce optimized collagen-like fibrillar assemblies for wound healing and other biomedical applications.

22 Claims, 16 Drawing Sheets

(56) References Cited

OTHER PUBLICATIONS

Barth, et al., The role of cystine knots in collagen folding and stability, Part II. Conformational properties of (Pro-Hyp-Gly)n model trimers with N- and C-terminal collagen type III cystein knots, Chemistry, 2003, 9(15), 3703-3714.
Berisio, et al., Crystal structure of the collagen triple helix model [(Pro-Pro-Gly)10]3, Protein Science, 2002, 11(2), 262-270.
Boudko, et al., Crystal structure of human type III collagen Gly991-Gly1032 cystine knot-containing peptide shows both 7/2 and 10/3 triple helical symmetries, J. Biol. Chem, 2008, 283, 32580-32589.
Horng, et al., Macrocyclic scaffold of the collagen triple helix, Organic Letters, 2006, 8(21), 4735-4738.
Huwiler, et al., Optimizing the MALDI-TOF-MS observation of peptides containing disulfide bonds, Journal of Biomolecular Techniques, 2003, 14, 289-297.
Jenkins and Raines, Insights on the conformational stability of collagen, Nat. Prod. Rep., 2002, 19, 49-59.
Jenkins, et al., Peptide bond isosteres: ester or (E)-alkene in the backbone of the collagen triple helix, Organic Letters, 2005, 7(13), 2619-2622.
Jones and Miller, Analysis of structural design features in collagen, J. Mol. Biol, 1991, 218, 209-219.
Khew, et al., Template-assembled triple-helical peptide molecules: mimicry of collagen by molecular architecture and integrin-specific cell adhesion, Biochemistry, 2008, 47(2), 585-596.
Kinberger, et al., Collagen mimetic dendrimers, J. Am. Chem. Soc., 2002, 124(51), 15162-15163.
Koide, et al., Self-complementary peptides for the formation of collagen-like triple helical supramolecules, Bioorg. Med. Chem. Let., 2005, 15(23), 5230-5233.
Kotch and Raines, Self-assembly of synthetic collagen triple helices, PNAS, 2006, 103(9), 3028-3033.
Lim, et al., Molecular dynamics for very large systems on massively parallel computers: the MPSim program, J. Compt. Chem., 1997, 18, 501-521.
Mayo, et al., Dreiding: A generic force field for molecular simulations, J. Phys. Chem., 1990, 94, 8897-8909.
Ottl and Moroder, Disulfide-bridged heterotrimeric collagen peptides containing the collagenase cleavage site of collagen typ I. Synthesis and conformational properties, J. Am. Chem. Soc., 1999, 121(4), 653-661.
Ozhogina and Bominaar, Characterization of the kringle fold and identification of a ubiquitous new class of disulfide rotamers, J. Struct. Biol., 2009, 168(2), 223-233.
Persikov, et al., Prediction of collagen stability from amino acid sequence, J. Biol. Chem., 2005, 280, 19343-19349.
Rabanal, et al., Use of 2,2'-dithiobis(5-nitropyridine) for the heterodimerizaton of cysteine containing peptides. Introduction of the 5-nitro-2-pyridinesulfenyl group, Tetrahedron Letters, 1996, 37(9), 1347-1350.
Shoulders and Raines, Collagen structure and stability, Annu. Rev. Biochem., 2009; 78, 929-958.
Wegener, et al., The cysteine-rich region of type VII collagen is a cystine knot with a new topology, J. Biol. Chem., 2014. 289, 4861-4869.
Word, et al., Asparagine and glutamine: using hydrogen atom contacts in the choice of side-chain amide orientation, J. Mol, Bio., 1999, 285(4), 1735-1747.
Yamazaki, et al., Artificial collagen gels via self-assembly of de novo designed peptides; Biopolymers, 2008, 90(6), 816-823.
Yamazaki, et al., A collagen-mimetic triple helical supramolecule that evokes integrin-dependent cell responses, Biomaterials, 2010, 31(7), 1925-1934.
Tanrikulu and Raines, Optimal interstrand Bridges for Collagen-like Biomaterials, JACS, Sep. 11, 2014, 136, 13490-13493.

* cited by examiner

```
                           SEQUENCE LISTING

<160> NUMBER OF SEQ ID NOS: 24

<210> SEQ ID NO 1
<211> LENGTH: 9
<212> TYPE: PRT
<213> ORGANISM: Artificial Sequence
<220> FEATURE:
<223> OTHER INFORMATION: Synthetic Collagen Mimic
<220> FEATURE:
<221> NAME/KEY: X
<222> LOCATION: (1)..(1)
<223> OTHER INFORMATION: Xaa is any amino acid
<220> FEATURE:
<221> NAME/KEY: X
<222> LOCATION: (2)..(2)
<223> OTHER INFORMATION: Xaa is any amino acid
<220> FEATURE:
<221> NAME/KEY: X
<222> LOCATION: (4)..(4)
<223> OTHER INFORMATION: Xaa is homocysteine
<220> FEATURE:
<221> NAME/KEY: X
<222> LOCATION: (5)..(5)
<223> OTHER INFORMATION: Xaa is any amino acid, but is the same amino
      acid as residue 2
<220> FEATURE:
<221> NAME/KEY: X
<222> LOCATION: (7)..(7)
<223> OTHER INFORMATION: Xaa is any amino acid, but is the same amino
      acid as residue 1
<220> FEATURE:
<221> NAME/KEY: X
<222> LOCATION: (8)..(8)
<223> OTHER INFORMATION: Xaa is any amino acid, but is the same amino
      acid as residue 2

<400> SEQUENCE: 1

Xaa Xaa Gly Xaa Xaa Gly Xaa Xaa Gly
1               5

<210> SEQ ID NO 2
<211> LENGTH: 9
<212> TYPE: PRT
<213> ORGANISM: Artificial Sequence
<220> FEATURE:
<223> OTHER INFORMATION: Synthetic Collagen Mimic
<220> FEATURE:
<221> NAME/KEY: Xaa
<222> LOCATION: (1)..(1)
<223> OTHER INFORMATION: Xaa is any amino acid
<220> FEATURE:
<221> NAME/KEY: Xaa
<222> LOCATION: (2)..(2)
<223> OTHER INFORMATION: Xaa is any amino acid
<220> FEATURE:
<221> NAME/KEY: Xaa
<222> LOCATION: (4)..(4)
<223> OTHER INFORMATION: Xaa is any amino acid, but is the same amino
      acid as residue 1
<220> FEATURE:
```

```
<221> NAME/KEY: Xaa
<222> LOCATION: (7)..(7)
<223> OTHER INFORMATION: Xaa is any amino acid, but is the same amino
      acid as residue 1
<220> FEATURE:
<221> NAME/KEY: Xaa
<222> LOCATION: (8)..(8)
<223> OTHER INFORMATION: Xaa is any amino acid, but is the same amino
      acid as residue 2

<400> SEQUENCE: 2

Xaa Xaa Gly Xaa Cys Gly Xaa Xaa Gly
1               5

<210> SEQ ID NO 3
<211> LENGTH: 15
<212> TYPE: PRT
<213> ORGANISM: Artificial Sequence
<220> FEATURE:
<223> OTHER INFORMATION: Synthetic Collagen Mimic
<220> FEATURE:
<221> NAME/KEY: Xaa
<222> LOCATION: (1)..(1)
<223> OTHER INFORMATION: Xaa is any amino acid
<220> FEATURE:
<221> NAME/KEY: Xaa
<222> LOCATION: (2)..(2)
<223> OTHER INFORMATION: Xaa is any amino acid
<220> FEATURE:
<221> NAME/KEY: Xaa
<222> LOCATION: (4)..(4)
<223> OTHER INFORMATION: Xaa is any amino acid, but is the same amino
      acid as residue 1
<220> FEATURE:
<221> NAME/KEY: Xaa
<222> LOCATION: (7)..(7)
<223> OTHER INFORMATION: Xaa is any amino acid, but is the same amino
      acid as residue 1
<220> FEATURE:
<221> NAME/KEY: Xaa
<222> LOCATION: (8)..(8)
<223> OTHER INFORMATION: Xaa is any amino acid, but is the same amino
      acid as residue 2
<220> FEATURE:
<221> NAME/KEY: Xaa
<222> LOCATION: (10)..(10)
<223> OTHER INFORMATION: Xaa is homocysteine
<220> FEATURE:
<221> NAME/KEY: Xaa
<222> LOCATION: (11)..(11)
<223> OTHER INFORMATION: Xaa is any amino acid, but is the same amino
      acid as residue 2
<220> FEATURE:
<221> NAME/KEY: Xaa
<222> LOCATION: (13)..(13)
<223> OTHER INFORMATION: Xaa is any amino acid, but is the same amino
      acid as residue 1
<220> FEATURE:
<221> NAME/KEY: Xaa
<222> LOCATION: (14)..(14)
<223> OTHER INFORMATION: Xaa is any amino acid, but is the same amino
      acid as residue 2

<400> SEQUENCE: 3

Xaa Xaa Gly Xaa Cys Gly Xaa Xaa Gly Xaa Xaa Gly Xaa Xaa Gly
1               5                   10                  15

<210> SEQ ID NO 4
<211> LENGTH: 15
<212> TYPE: PRT
<213> ORGANISM: Artificial Sequence
<220> FEATURE:
<223> OTHER INFORMATION: Synthetic Collagen Mimic
<220> FEATURE:
<221> NAME/KEY: Xaa
```

```
<222> LOCATION: (1)..(1)
<223> OTHER INFORMATION: Xaa is any amino acid
<220> FEATURE:
<221> NAME/KEY: Xaa
<222> LOCATION: (2)..(2)
<223> OTHER INFORMATION: Xaa is any amino acid
<220> FEATURE:
<221> NAME/KEY: Xaa
<222> LOCATION: (4)..(4)
<223> OTHER INFORMATION: Xaa is homocysteine
<220> FEATURE:
<221> NAME/KEY: Xaa
<222> LOCATION: (5)..(5)
<223> OTHER INFORMATION: Xaa is any amino acid, but is the same amino
      acid as residue 2
<220> FEATURE:
<221> NAME/KEY: Xaa
<222> LOCATION: (7)..(7)
<223> OTHER INFORMATION: Xaa is any amino acid, but is the same amino
      acid as residue 1
<220> FEATURE:
<221> NAME/KEY: Xaa
<222> LOCATION: (8)..(8)
<223> OTHER INFORMATION: Xaa is any amino acid, but is the same amino
      acid as residue 2
<220> FEATURE:
<221> NAME/KEY: Xaa
<222> LOCATION: (10)..(10)
<223> OTHER INFORMATION: Xaa is any amino acid, but is the same amino
      acid as residue 1
<220> FEATURE:
<221> NAME/KEY: Xaa
<222> LOCATION: (13)..(13)
<223> OTHER INFORMATION: Xaa is any amino acid, but is the same amino
      acid as residue 1
<220> FEATURE:
<221> NAME/KEY: Xaa
<222> LOCATION: (14)..(14)
<223> OTHER INFORMATION: Xaa is any amino acid, but is the same amino
      acid as residue 2

<400> SEQUENCE: 4

Xaa Xaa Gly Xaa Xaa Gly Xaa Xaa Gly Xaa Cys Gly Xaa Xaa Gly
1               5                   10                  15

<210> SEQ ID NO 5
<211> LENGTH: 30
<212> TYPE: PRT
<213> ORGANISM: Artificial Sequence
<220> FEATURE:
<223> OTHER INFORMATION: Synthetic Collagen Mimic
<220> FEATURE:
<221> NAME/KEY: Xaa
<222> LOCATION: (16)..(16)
<223> OTHER INFORMATION: Xaa is either Cysteine or Homocysteine

<400> SEQUENCE: 5

Pro Pro Gly Pro Pro Gly Pro Pro Gly Pro Pro Gly Pro Pro Gly Xaa
1               5                   10                  15

Pro Gly Pro Pro Gly Pro Pro Gly Pro Pro Gly Pro Pro Gly
            20                  25                  30

<210> SEQ ID NO 6
<211> LENGTH: 30
<212> TYPE: PRT
<213> ORGANISM: Artificial Sequence
<220> FEATURE:
<223> OTHER INFORMATION: Synthetic Collagen Mimic

<400> SEQUENCE: 6

Pro Pro Gly Pro Pro Gly Pro Pro Gly Pro Pro Gly Pro Pro Gly Pro
1               5                   10                  15
```

Pro Gly Pro Pro Gly Pro Pro Gly Pro Pro Gly
            20              25              30

<210> SEQ ID NO 7
<211> LENGTH: 30
<212> TYPE: PRT
<213> ORGANISM: Artificial Sequence
<220> FEATURE:
<223> OTHER INFORMATION: Synthetic Collagen Mimic
<220> FEATURE:
<221> NAME/KEY: Xaa
<222> LOCATION: (14)..(14)
<223> OTHER INFORMATION: Xaa is either cysteine or homocysteine

<400> SEQUENCE: 7

Pro Pro Gly Pro Pro Gly Pro Pro Gly Pro Pro Gly Pro Xaa Gly Pro
1               5                   10                  15

Pro Gly Pro Pro Gly Pro Pro Gly Pro Pro Gly Pro Pro Gly
            20              25              30

<210> SEQ ID NO 8
<211> LENGTH: 24
<212> TYPE: PRT
<213> ORGANISM: Artificial Sequence
<220> FEATURE:
<223> OTHER INFORMATION: Synthetic Collagen Mimic
<220> FEATURE:
<221> NAME/KEY: Pro
<222> LOCATION: (2)..(2)
<223> OTHER INFORMATION: Pro is hydroxyproline
<220> FEATURE:
<221> NAME/KEY: Pro
<222> LOCATION: (5)..(5)
<223> OTHER INFORMATION: Pro is hydroxyproline
<220> FEATURE:
<221> NAME/KEY: Pro
<222> LOCATION: (8)..(8)
<223> OTHER INFORMATION: Pro is hydroxyproline
<220> FEATURE:
<221> NAME/KEY: Pro
<222> LOCATION: (11)..(11)
<223> OTHER INFORMATION: Pro is hydroxyproline
<220> FEATURE:
<221> NAME/KEY: Pro
<222> LOCATION: (14)..(14)
<223> OTHER INFORMATION: Pro is hydroxyproline
<220> FEATURE:
<221> NAME/KEY: Xaa
<222> LOCATION: (16)..(16)
<223> OTHER INFORMATION: Xaa is homocysteine
<220> FEATURE:
<221> NAME/KEY: Pro
<222> LOCATION: (17)..(17)
<223> OTHER INFORMATION: Pro is hydroxyproline
<220> FEATURE:
<221> NAME/KEY: Pro
<222> LOCATION: (20)..(20)
<223> OTHER INFORMATION: Pro is hydroxyproline
<220> FEATURE:
<221> NAME/KEY: Pro
<222> LOCATION: (23)..(23)
<223> OTHER INFORMATION: Pro is hydroxyproline

<400> SEQUENCE: 8

Pro Pro Gly Pro Pro Gly Pro Pro Gly Pro Pro Gly Pro Pro Gly Xaa
1               5                   10                  15

Pro Gly Pro Pro Gly Pro Pro Gly
            20

<210> SEQ ID NO 9
<211> LENGTH: 24
<212> TYPE: PRT

```
<213> ORGANISM: Artificial Sequence
<220> FEATURE:
<223> OTHER INFORMATION: Synthetic Collagen Mimic
<220> FEATURE:
<221> NAME/KEY: Pro
<222> LOCATION: (2)..(2)
<223> OTHER INFORMATION: Pro is hydroxyproline
<220> FEATURE:
<221> NAME/KEY: Pro
<222> LOCATION: (5)..(5)
<223> OTHER INFORMATION: Pro is hydroxyproline
<220> FEATURE:
<221> NAME/KEY: Pro
<222> LOCATION: (11)..(11)
<223> OTHER INFORMATION: Pro is hydroxyproline
<220> FEATURE:
<221> NAME/KEY: Pro
<222> LOCATION: (14)..(14)
<223> OTHER INFORMATION: Pro is hydroxyproline
<220> FEATURE:
<221> NAME/KEY: Pro
<222> LOCATION: (17)..(17)
<223> OTHER INFORMATION: Pro is hydroxyproline
<220> FEATURE:
<221> NAME/KEY: Pro
<222> LOCATION: (20)..(20)
<223> OTHER INFORMATION: Pro is hydroxyproline
<220> FEATURE:
<221> NAME/KEY: Pro
<222> LOCATION: (23)..(23)
<223> OTHER INFORMATION: Pro is hydroxyproline

<400> SEQUENCE: 9

Pro Pro Gly Pro Pro Gly Pro Cys Gly Pro Pro Gly Pro Pro Gly Pro
1               5                   10                  15

Pro Gly Pro Pro Gly Pro Pro Gly
            20

<210> SEQ ID NO 10
<211> LENGTH: 24
<212> TYPE: PRT
<213> ORGANISM: Artificial Sequence
<220> FEATURE:
<223> OTHER INFORMATION: Synthetic Collagen Mimic
<220> FEATURE:
<221> NAME/KEY: Pro
<222> LOCATION: (2)..(2)
<223> OTHER INFORMATION: Pro is hydroxyproline
<220> FEATURE:
<221> NAME/KEY: Pro
<222> LOCATION: (5)..(5)
<223> OTHER INFORMATION: Pro is hydroxyproline
<220> FEATURE:
<221> NAME/KEY: Pro
<222> LOCATION: (8)..(8)
<223> OTHER INFORMATION: Pro is hydroxyproline
<220> FEATURE:
<221> NAME/KEY: Pro
<222> LOCATION: (11)..(11)
<223> OTHER INFORMATION: Pro is hydroxyproline
<220> FEATURE:
<221> NAME/KEY: Pro
<222> LOCATION: (14)..(14)
<223> OTHER INFORMATION: Pro is hydroxyproline
<220> FEATURE:
<221> NAME/KEY: Xaa
<222> LOCATION: (16)..(16)
<223> OTHER INFORMATION: Xaa is homocysteine
<220> FEATURE:
<221> NAME/KEY: Pro
<222> LOCATION: (17)..(17)
<223> OTHER INFORMATION: Pro is hydroxyproline
<220> FEATURE:
<221> NAME/KEY: Pro
<222> LOCATION: (20)..(20)
<223> OTHER INFORMATION: Pro is hydroxyproline
```

```
<220> FEATURE:
<221> NAME/KEY: Pro
<222> LOCATION: (23)..(23)
<223> OTHER INFORMATION: Pro is hydroxyproline

<400> SEQUENCE: 10

Pro Pro Gly Pro Pro Gly Pro Pro Gly Pro Pro Gly Pro Pro Gly Xaa
1               5                   10                  15

Pro Gly Pro Pro Gly Pro Pro Gly
            20

<210> SEQ ID NO 11
<211> LENGTH: 48
<212> TYPE: PRT
<213> ORGANISM: Artificial Sequence
<220> FEATURE:
<223> OTHER INFORMATION: Synthetic Collagen Mimic
<220> FEATURE:
<221> NAME/KEY: Pro
<222> LOCATION: (2)..(2)
<223> OTHER INFORMATION: Pro is hydroxyproliine
<220> FEATURE:
<221> NAME/KEY: Pro
<222> LOCATION: (5)..(5)
<223> OTHER INFORMATION: Pro is hydroxyproliine
<220> FEATURE:
<221> NAME/KEY: Pro
<222> LOCATION: (8)..(8)
<223> OTHER INFORMATION: Pro is hydroxyproliine
<220> FEATURE:
<221> NAME/KEY: Pro
<222> LOCATION: (11)..(11)
<223> OTHER INFORMATION: Pro is hydroxyproliine
<220> FEATURE:
<221> NAME/KEY: Pro
<222> LOCATION: (14)..(14)
<223> OTHER INFORMATION: Pro is hydroxyproliine
<220> FEATURE:
<221> NAME/KEY: Xaa
<222> LOCATION: (16)..(16)
<223> OTHER INFORMATION: Xaa is homocysteine
<220> FEATURE:
<221> NAME/KEY: Pro
<222> LOCATION: (17)..(17)
<223> OTHER INFORMATION: Pro is hydroxyproline
<220> FEATURE:
<221> NAME/KEY: Pro
<222> LOCATION: (20)..(20)
<223> OTHER INFORMATION: Pro is hydroxyproline
<220> FEATURE:
<221> NAME/KEY: Pro
<222> LOCATION: (23)..(23)
<223> OTHER INFORMATION: Pro is hydroxyproline
<220> FEATURE:
<221> NAME/KEY: Pro
<222> LOCATION: (26)..(26)
<223> OTHER INFORMATION: Pro is hydroxyproline
<220> FEATURE:
<221> NAME/KEY: Pro
<222> LOCATION: (29)..(29)
<223> OTHER INFORMATION: Pro is hydroxyproline
<220> FEATURE:
<221> NAME/KEY: Pro
<222> LOCATION: (35)..(35)
<223> OTHER INFORMATION: Pro is hydroxyproline
<220> FEATURE:
<221> NAME/KEY: Pro
<222> LOCATION: (38)..(38)
<223> OTHER INFORMATION: Pro is hydroxyproline
<220> FEATURE:
<221> NAME/KEY: Pro
<222> LOCATION: (41)..(41)
<223> OTHER INFORMATION: Pro is hydroxyproline
<220> FEATURE:
<221> NAME/KEY: Pro
<222> LOCATION: (44)..(44)
```

```
<223> OTHER INFORMATION: Pro is hydroxyproline
<220> FEATURE:
<221> NAME/KEY: Pro
<222> LOCATION: (47)..(47)
<223> OTHER INFORMATION: Pro is hydroxyproline

<400> SEQUENCE: 11

Pro Pro Gly Pro Pro Gly Pro Pro Gly Pro Pro Gly Pro Pro Gly Xaa
1               5                   10                  15

Pro Gly Pro Pro Gly Pro Pro Gly Pro Pro Gly Pro Pro Gly Pro Cys
            20                  25                  30

Gly Pro Pro Gly Pro Pro Gly Pro Pro Gly Pro Pro Gly Pro Pro Gly
        35                  40                  45

<210> SEQ ID NO 12
<211> LENGTH: 24
<212> TYPE: PRT
<213> ORGANISM: Artificial Sequence
<220> FEATURE:
<223> OTHER INFORMATION: Synthetic Collagen Mimic
<220> FEATURE:
<221> NAME/KEY: Pro
<222> LOCATION: (2)..(2)
<223> OTHER INFORMATION: Pro is hydroxyproline
<220> FEATURE:
<221> NAME/KEY: Pro
<222> LOCATION: (5)..(5)
<223> OTHER INFORMATION: Pro is hydroxyproline
<220> FEATURE:
<221> NAME/KEY: Pro
<222> LOCATION: (11)..(11)
<223> OTHER INFORMATION: Pro is hydroxyproline
<220> FEATURE:
<221> NAME/KEY: Pro
<222> LOCATION: (14)..(14)
<223> OTHER INFORMATION: Pro is hydroxyproline
<220> FEATURE:
<221> NAME/KEY: Pro
<222> LOCATION: (17)..(17)
<223> OTHER INFORMATION: Pro is hydroxyproline
<220> FEATURE:
<221> NAME/KEY: Pro
<222> LOCATION: (20)..(20)
<223> OTHER INFORMATION: Pro is hydroxyproline
<220> FEATURE:
<221> NAME/KEY: Pro
<222> LOCATION: (23)..(23)
<223> OTHER INFORMATION: Pro is hydroxyproline
<220> FEATURE:
<221> NAME/KEY: Pro
<222> LOCATION: (24)..(24)
<223> OTHER INFORMATION: Pro is hydroxyproline

<400> SEQUENCE: 12

Pro Pro Gly Pro Pro Gly Pro Cys Gly Pro Pro Gly Pro Pro Gly Pro
1               5                   10                  15

Pro Gly Pro Pro Gly Pro Pro Gly
            20

<210> SEQ ID NO 13
<211> LENGTH: 96
<212> TYPE: PRT
<213> ORGANISM: Artificial Sequence
<220> FEATURE:
<223> OTHER INFORMATION: Synthetic Collagen Mimic
<220> FEATURE:
<221> NAME/KEY: Pro
<222> LOCATION: (2)..(2)
<223> OTHER INFORMATION: Pro is hydroxyproline
<220> FEATURE:
<221> NAME/KEY: Pro
<222> LOCATION: (5)..(5)
```

```
<223> OTHER INFORMATION: Pro is hydroxyproline
<220> FEATURE:
<221> NAME/KEY: Pro
<222> LOCATION: (8)..(8)
<223> OTHER INFORMATION: Pro is hydroxyproline
<220> FEATURE:
<221> NAME/KEY: Pro
<222> LOCATION: (11)..(11)
<223> OTHER INFORMATION: Pro is hydroxyproline
<220> FEATURE:
<221> NAME/KEY: Pro
<222> LOCATION: (14)..(14)
<223> OTHER INFORMATION: Pro is hydroxyproline
<220> FEATURE:
<221> NAME/KEY: Xaa
<222> LOCATION: (16)..(16)
<223> OTHER INFORMATION: Xaa is homocysteine
<220> FEATURE:
<221> NAME/KEY: Pro
<222> LOCATION: (17)..(17)
<223> OTHER INFORMATION: Pro is hydroxyproline
<220> FEATURE:
<221> NAME/KEY: Pro
<222> LOCATION: (20)..(20)
<223> OTHER INFORMATION: Pro is hydroxyproline
<220> FEATURE:
<221> NAME/KEY: Pro
<222> LOCATION: (23)..(23)
<223> OTHER INFORMATION: Pro is hydroxyproline
<220> FEATURE:
<221> NAME/KEY: Pro
<222> LOCATION: (26)..(26)
<223> OTHER INFORMATION: Pro is hydroxyproline
<220> FEATURE:
<221> NAME/KEY: Pro
<222> LOCATION: (29)..(29)
<223> OTHER INFORMATION: Pro is hydroxyproline
<220> FEATURE:
<221> NAME/KEY: Pro
<222> LOCATION: (35)..(35)
<223> OTHER INFORMATION: Pro is hydroxyproline
<220> FEATURE:
<221> NAME/KEY: Pro
<222> LOCATION: (38)..(38)
<223> OTHER INFORMATION: Pro is hydroxyproline
<220> FEATURE:
<221> NAME/KEY: Pro
<222> LOCATION: (41)..(41)
<223> OTHER INFORMATION: Pro is hydroxyproline
<220> FEATURE:
<221> NAME/KEY: Pro
<222> LOCATION: (44)..(44)
<223> OTHER INFORMATION: Pro is hydroxyproline
<220> FEATURE:
<221> NAME/KEY: Pro
<222> LOCATION: (47)..(47)
<223> OTHER INFORMATION: Pro is hydroxyproline
<220> FEATURE:
<221> NAME/KEY: Pro
<222> LOCATION: (50)..(50)
<223> OTHER INFORMATION: Pro is hydroxyproline
<220> FEATURE:
<221> NAME/KEY: Pro
<222> LOCATION: (53)..(53)
<223> OTHER INFORMATION: Pro is hydroxyproline
<220> FEATURE:
<221> NAME/KEY: Pro
<222> LOCATION: (56)..(56)
<223> OTHER INFORMATION: Pro is hydroxyproline
<220> FEATURE:
<221> NAME/KEY: Pro
<222> LOCATION: (59)..(59)
<223> OTHER INFORMATION: Pro is hydroxyproline
<220> FEATURE:
<221> NAME/KEY: Pro
<222> LOCATION: (62)..(62)
<223> OTHER INFORMATION: Pro is hydroxyproline
<220> FEATURE:
<221> NAME/KEY: Xaa
```

```
<222> LOCATION: (64)..(64)
<223> OTHER INFORMATION: Xaa is homocysteine
<220> FEATURE:
<221> NAME/KEY: Pro
<222> LOCATION: (65)..(65)
<223> OTHER INFORMATION: Pro is hydroxyproline
<220> FEATURE:
<221> NAME/KEY: Pro
<222> LOCATION: (68)..(68)
<223> OTHER INFORMATION: Pro is hydroxyproline
<220> FEATURE:
<221> NAME/KEY: Pro
<222> LOCATION: (71)..(71)
<223> OTHER INFORMATION: Pro is hydroxyproline
<220> FEATURE:
<221> NAME/KEY: Pro
<222> LOCATION: (74)..(74)
<223> OTHER INFORMATION: Pro is hydroxyproline
<220> FEATURE:
<221> NAME/KEY: Pro
<222> LOCATION: (77)..(77)
<223> OTHER INFORMATION: Pro is hydroxyproline
<220> FEATURE:
<221> NAME/KEY: Pro
<222> LOCATION: (83)..(83)
<223> OTHER INFORMATION: Pro is hydroxyproline
<220> FEATURE:
<221> NAME/KEY: Pro
<222> LOCATION: (86)..(86)
<223> OTHER INFORMATION: Pro is hydroxyproline
<220> FEATURE:
<221> NAME/KEY: Pro
<222> LOCATION: (89)..(89)
<223> OTHER INFORMATION: Pro is hydroxyproline
<220> FEATURE:
<221> NAME/KEY: Pro
<222> LOCATION: (92)..(92)
<223> OTHER INFORMATION: Pro is hydroxyproline
<220> FEATURE:
<221> NAME/KEY: Pro
<222> LOCATION: (95)..(95)
<223> OTHER INFORMATION: Pro is hydroxyproline

<400> SEQUENCE: 13

Pro Pro Gly Pro Pro Gly Pro Pro Gly Pro Pro Gly Pro Pro Gly Xaa
1               5                   10                  15

Pro Gly Pro Pro Gly Pro Pro Gly Pro Pro Gly Pro Pro Gly Pro Cys
            20                  25                  30

Gly Pro Pro Gly Pro Pro Gly Pro Pro Gly Pro Pro Gly Pro Pro Gly
        35                  40                  45

Pro Pro Gly Pro Pro Gly Pro Pro Gly Pro Pro Gly Pro Pro Gly Xaa
    50                  55                  60

Pro Gly Pro Pro Gly Pro Pro Gly Pro Pro Gly Pro Pro Gly Pro Cys
65              70                  75                  80

Gly Pro Pro Gly Pro Pro Gly Pro Pro Gly Pro Pro Gly Pro Pro Gly
            85                  90                  95

<210> SEQ ID NO 14
<211> LENGTH: 96
<212> TYPE: PRT
<213> ORGANISM: Artificial Sequence
<220> FEATURE:
<223> OTHER INFORMATION: Synthetic Collagen Mimic
<220> FEATURE:
<221> NAME/KEY: Pro
<222> LOCATION: (2)..(2)
<223> OTHER INFORMATION: Pro is hydroxyproline
<220> FEATURE:
<221> NAME/KEY: Pro
<222> LOCATION: (5)..(5)
<223> OTHER INFORMATION: Pro is hydroxyproline
<220> FEATURE:
```

```
<221> NAME/KEY: Pro
<222> LOCATION: (11)..(11)
<223> OTHER INFORMATION: Pro is hydroxyproline
<220> FEATURE:
<221> NAME/KEY: Pro
<222> LOCATION: (14)..(14)
<223> OTHER INFORMATION: Pro is hydroxyproline
<220> FEATURE:
<221> NAME/KEY: Pro
<222> LOCATION: (17)..(17)
<223> OTHER INFORMATION: Pro is hydroxyproline
<220> FEATURE:
<221> NAME/KEY: Pro
<222> LOCATION: (20)..(20)
<223> OTHER INFORMATION: Pro is hydroxyproline
<220> FEATURE:
<221> NAME/KEY: Pro
<222> LOCATION: (23)..(23)
<223> OTHER INFORMATION: Pro is hydroxyproline
<220> FEATURE:
<221> NAME/KEY: Pro
<222> LOCATION: (26)..(26)
<223> OTHER INFORMATION: Pro is hydroxyproline
<220> FEATURE:
<221> NAME/KEY: Pro
<222> LOCATION: (29)..(29)
<223> OTHER INFORMATION: Pro is hydroxyproline
<220> FEATURE:
<221> NAME/KEY: Pro
<222> LOCATION: (32)..(32)
<223> OTHER INFORMATION: Pro is hydroxyproline
<220> FEATURE:
<221> NAME/KEY: Pro
<222> LOCATION: (35)..(35)
<223> OTHER INFORMATION: Pro is hydroxyproline
<220> FEATURE:
<221> NAME/KEY: Pro
<222> LOCATION: (38)..(38)
<223> OTHER INFORMATION: Pro is hydroxyproline
<220> FEATURE:
<221> NAME/KEY: Xaa
<222> LOCATION: (40)..(40)
<223> OTHER INFORMATION: Xaa is homocysteine
<220> FEATURE:
<221> NAME/KEY: Pro
<222> LOCATION: (41)..(41)
<223> OTHER INFORMATION: Pro is hydroxyproline
<220> FEATURE:
<221> NAME/KEY: Pro
<222> LOCATION: (44)..(44)
<223> OTHER INFORMATION: Pro is hydroxyproline
<220> FEATURE:
<221> NAME/KEY: Pro
<222> LOCATION: (47)..(47)
<223> OTHER INFORMATION: Pro is hydroxyproline
<220> FEATURE:
<221> NAME/KEY: Pro
<222> LOCATION: (50)..(50)
<223> OTHER INFORMATION: Pro is hydroxyproline
<220> FEATURE:
<221> NAME/KEY: Pro
<222> LOCATION: (53)..(53)
<223> OTHER INFORMATION: Pro is hydroxyproline
<220> FEATURE:
<221> NAME/KEY: Pro
<222> LOCATION: (59)..(59)
<223> OTHER INFORMATION: Pro is hydroxyproline
<220> FEATURE:
<221> NAME/KEY: Pro
<222> LOCATION: (62)..(62)
<223> OTHER INFORMATION: Pro is hydroxyproline
<220> FEATURE:
<221> NAME/KEY: Pro
<222> LOCATION: (65)..(65)
<223> OTHER INFORMATION: Pro is hydroxyproline
<220> FEATURE:
<221> NAME/KEY: Pro
<222> LOCATION: (68)..(68)
<223> OTHER INFORMATION: Pro is hydroxyproline
```

```
<220> FEATURE:
<221> NAME/KEY: Pro
<222> LOCATION: (71)..(71)
<223> OTHER INFORMATION: Pro is hydroxyproline
<220> FEATURE:
<221> NAME/KEY: Pro
<222> LOCATION: (74)..(74)
<223> OTHER INFORMATION: Pro is hydroxyproline
<220> FEATURE:
<221> NAME/KEY: Pro
<222> LOCATION: (77)..(77)
<223> OTHER INFORMATION: Pro is hydroxyproline
<220> FEATURE:
<221> NAME/KEY: Pro
<222> LOCATION: (80)..(80)
<223> OTHER INFORMATION: Pro is hydroxyproline
<220> FEATURE:
<221> NAME/KEY: Pro
<222> LOCATION: (83)..(83)
<223> OTHER INFORMATION: Pro is hydroxyproline
<220> FEATURE:
<221> NAME/KEY: Pro
<222> LOCATION: (86)..(86)
<223> OTHER INFORMATION: Pro is hydroxyproline
<220> FEATURE:
<221> NAME/KEY: Xaa
<222> LOCATION: (88)..(88)
<223> OTHER INFORMATION: Xaa is homocysteine
<220> FEATURE:
<221> NAME/KEY: Pro
<222> LOCATION: (89)..(89)
<223> OTHER INFORMATION: Pro is hydroxyproline
<220> FEATURE:
<221> NAME/KEY: Pro
<222> LOCATION: (92)..(92)
<223> OTHER INFORMATION: Pro is hydroxyproline
<220> FEATURE:
<221> NAME/KEY: Pro
<222> LOCATION: (95)..(95)
<223> OTHER INFORMATION: Pro is hydroxyproline

<400> SEQUENCE: 14

Pro Pro Gly Pro Pro Gly Pro Cys Gly Pro Pro Gly Pro Pro Gly Pro
1               5                   10                  15

Pro Gly Pro Pro Gly Pro Pro Gly Pro Pro Gly Pro Pro Gly Pro Pro
                20                  25                  30

Gly Pro Pro Gly Pro Pro Gly Xaa Pro Gly Pro Pro Gly Pro Pro Gly
            35                  40                  45

Pro Pro Gly Pro Pro Gly Pro Cys Gly Pro Pro Gly Pro Pro Gly Pro
        50                  55                  60

Pro Gly Pro Pro Gly Pro Pro Gly Pro Pro Gly Pro Pro Gly Pro Pro
65                  70                  75                  80

Gly Pro Pro Gly Pro Pro Gly Xaa Pro Gly Pro Pro Gly Pro Pro Gly
                85                  90                  95

<210> SEQ ID NO 15
<211> LENGTH: 24
<212> TYPE: PRT
<213> ORGANISM: Artificial Sequence
<220> FEATURE:
<223> OTHER INFORMATION: Synthetic Collagen Mimic
<220> FEATURE:
<221> NAME/KEY: Pro
<222> LOCATION: (2)..(2)
<223> OTHER INFORMATION: Pro is hydroxyproline
<220> FEATURE:
<221> NAME/KEY: Pro
<222> LOCATION: (5)..(5)
<223> OTHER INFORMATION: Pro is hydroxyproline
<220> FEATURE:
<221> NAME/KEY: Pro
<222> LOCATION: (8)..(8)
```

```
<223> OTHER INFORMATION: Pro is hydroxyproline
<220> FEATURE:
<221> NAME/KEY: Pro
<222> LOCATION: (11)..(11)
<223> OTHER INFORMATION: Pro is hydroxyproline
<220> FEATURE:
<221> NAME/KEY: Pro
<222> LOCATION: (14)..(14)
<223> OTHER INFORMATION: Pro is hydroxyproline
<220> FEATURE:
<221> NAME/KEY: Pro
<222> LOCATION: (17)..(17)
<223> OTHER INFORMATION: Pro is hydroxyproline
<220> FEATURE:
<221> NAME/KEY: Pro
<222> LOCATION: (20)..(20)
<223> OTHER INFORMATION: Pro is hydroxyproline
<220> FEATURE:
<221> NAME/KEY: Pro
<222> LOCATION: (23)..(23)
<223> OTHER INFORMATION: Pro is hydroxyproline

<400> SEQUENCE: 15

Pro Pro Gly Pro Pro Gly Pro Pro Gly Pro Pro Gly Pro Pro Gly Pro
1               5                   10                  15

Pro Gly Pro Pro Gly Pro Pro Gly
            20

<210> SEQ ID NO 16
<211> LENGTH: 135
<212> TYPE: PRT
<213> ORGANISM: Artificial Sequence
<220> FEATURE:
<223> OTHER INFORMATION: Synthetic Collagen Mimic
<220> FEATURE:
<221> NAME/KEY: Pro
<222> LOCATION: (2)..(2)
<223> OTHER INFORMATION: Pro is hydroxyproline
<220> FEATURE:
<221> NAME/KEY: Pro
<222> LOCATION: (5)..(5)
<223> OTHER INFORMATION: Pro is hydroxyproline
<220> FEATURE:
<221> NAME/KEY: Pro
<222> LOCATION: (8)..(8)
<223> OTHER INFORMATION: Pro is hydroxyproline
<220> FEATURE:
<221> NAME/KEY: Pro
<222> LOCATION: (11)..(11)
<223> OTHER INFORMATION: Pro is hydroxyproline
<220> FEATURE:
<221> NAME/KEY: Pro
<222> LOCATION: (14)..(14)
<223> OTHER INFORMATION: Pro is hydroxyproline
<220> FEATURE:
<221> NAME/KEY: Pro
<222> LOCATION: (17)..(17)
<223> OTHER INFORMATION: Pro is hydroxyproline
<220> FEATURE:
<221> NAME/KEY: Pro
<222> LOCATION: (20)..(20)
<223> OTHER INFORMATION: Pro is hydroxyproline
<220> FEATURE:
<221> NAME/KEY: Pro
<222> LOCATION: (23)..(23)
<223> OTHER INFORMATION: Pro is hydroxyproline
<220> FEATURE:
<221> NAME/KEY: Pro
<222> LOCATION: (26)..(26)
<223> OTHER INFORMATION: Pro is hydroxyproline
<220> FEATURE:
<221> NAME/KEY: Pro
<222> LOCATION: (29)..(29)
<223> OTHER INFORMATION: Pro is hydroxyproline
<220> FEATURE:
<221> NAME/KEY: Pro
```

```
<222> LOCATION: (32)..(32)
<223> OTHER INFORMATION: Pro is hydroxyproline
<220> FEATURE:
<221> NAME/KEY: Pro
<222> LOCATION: (35)..(35)
<223> OTHER INFORMATION: Pro is hydroxyproline
<220> FEATURE:
<221> NAME/KEY: Pro
<222> LOCATION: (38)..(38)
<223> OTHER INFORMATION: Pro is hydroxyproline
<220> FEATURE:
<221> NAME/KEY: Pro
<222> LOCATION: (41)..(41)
<223> OTHER INFORMATION: Pro is hydroxyproline
<220> FEATURE:
<221> NAME/KEY: Pro
<222> LOCATION: (44)..(44)
<223> OTHER INFORMATION: Pro is hydroxyproline
<220> FEATURE:
<221> NAME/KEY: Pro
<222> LOCATION: (47)..(47)
<223> OTHER INFORMATION: Pro is hydroxyproline
<220> FEATURE:
<221> NAME/KEY: Pro
<222> LOCATION: (50)..(50)
<223> OTHER INFORMATION: Pro is hydroxyproline
<220> FEATURE:
<221> NAME/KEY: Pro
<222> LOCATION: (53)..(53)
<223> OTHER INFORMATION: Pro is hydroxyproline
<220> FEATURE:
<221> NAME/KEY: Pro
<222> LOCATION: (56)..(56)
<223> OTHER INFORMATION: Pro is hydroxyproline
<220> FEATURE:
<221> NAME/KEY: Pro
<222> LOCATION: (59)..(59)
<223> OTHER INFORMATION: Pro is hydroxyproline
<220> FEATURE:
<221> NAME/KEY: Pro
<222> LOCATION: (62)..(62)
<223> OTHER INFORMATION: Pro is hydroxyproline
<220> FEATURE:
<221> NAME/KEY: Pro
<222> LOCATION: (65)..(65)
<223> OTHER INFORMATION: Pro is hydroxyproline
<220> FEATURE:
<221> NAME/KEY: Pro
<222> LOCATION: (68)..(68)
<223> OTHER INFORMATION: Pro is hydroxyproline
<220> FEATURE:
<221> NAME/KEY: Pro
<222> LOCATION: (71)..(71)
<223> OTHER INFORMATION: Pro is hydroxyproline
<220> FEATURE:
<221> NAME/KEY: Pro
<222> LOCATION: (74)..(74)
<223> OTHER INFORMATION: Pro is hydroxyproline
<220> FEATURE:
<221> NAME/KEY: Pro
<222> LOCATION: (77)..(77)
<223> OTHER INFORMATION: Pro is hydroxyproline
<220> FEATURE:
<221> NAME/KEY: Pro
<222> LOCATION: (80)..(80)
<223> OTHER INFORMATION: Pro is hydroxyproline
<220> FEATURE:
<221> NAME/KEY: Pro
<222> LOCATION: (83)..(83)
<223> OTHER INFORMATION: Pro is hydroxyproline
<220> FEATURE:
<221> NAME/KEY: Pro
<222> LOCATION: (86)..(86)
<223> OTHER INFORMATION: Pro is hydroxyproline
<220> FEATURE:
<221> NAME/KEY: Pro
<222> LOCATION: (89)..(89)
<223> OTHER INFORMATION: Pro is hydroxyproline
<220> FEATURE:
```

```
<221> NAME/KEY: Pro
<222> LOCATION: (92)..(92)
<223> OTHER INFORMATION: Pro is hydroxyproline
<220> FEATURE:
<221> NAME/KEY: Pro
<222> LOCATION: (95)..(95)
<223> OTHER INFORMATION: Pro is hydroxyproline
<220> FEATURE:
<221> NAME/KEY: Pro
<222> LOCATION: (98)..(98)
<223> OTHER INFORMATION: Pro is hydroxyproline
<220> FEATURE:
<221> NAME/KEY: Pro
<222> LOCATION: (101)..(101)
<223> OTHER INFORMATION: Pro is hydroxyproline
<220> FEATURE:
<221> NAME/KEY: Pro
<222> LOCATION: (104)..(104)
<223> OTHER INFORMATION: Pro is hydroxyproline
<220> FEATURE:
<221> NAME/KEY: Pro
<222> LOCATION: (107)..(107)
<223> OTHER INFORMATION: Pro is hydroxyproline
<220> FEATURE:
<221> NAME/KEY: Pro
<222> LOCATION: (110)..(110)
<223> OTHER INFORMATION: Pro is hydroxyproline
<220> FEATURE:
<221> NAME/KEY: Pro
<222> LOCATION: (113)..(113)
<223> OTHER INFORMATION: Pro is hydroxyproline
<220> FEATURE:
<221> NAME/KEY: Pro
<222> LOCATION: (116)..(116)
<223> OTHER INFORMATION: Pro is hydroxyproline
<220> FEATURE:
<221> NAME/KEY: Pro
<222> LOCATION: (119)..(119)
<223> OTHER INFORMATION: Pro is hydroxyproline
<220> FEATURE:
<221> NAME/KEY: Pro
<222> LOCATION: (122)..(122)
<223> OTHER INFORMATION: Pro is hydroxyproline
<220> FEATURE:
<221> NAME/KEY: Pro
<222> LOCATION: (125)..(125)
<223> OTHER INFORMATION: Pro is hydroxyproline
<220> FEATURE:
<221> NAME/KEY: Pro
<222> LOCATION: (128)..(128)
<223> OTHER INFORMATION: Pro is hydroxyproline
<220> FEATURE:
<221> NAME/KEY: Pro
<222> LOCATION: (131)..(131)
<223> OTHER INFORMATION: Pro is hydroxyproline
<220> FEATURE:
<221> NAME/KEY: Pro
<222> LOCATION: (134)..(134)
<223> OTHER INFORMATION: Pro is hydroxyproline

<400> SEQUENCE: 16

Pro Pro Gly Pro Pro Gly Pro Pro Gly Pro Pro Gly Pro Pro Gly Pro
1               5                   10                  15

Pro Gly Pro Pro Gly Pro Pro Gly Pro Pro Gly Pro Pro Gly Pro Pro
            20                  25                  30

Gly Pro Pro Gly Pro Pro Gly Pro Pro Gly Pro Pro Gly Pro Pro Gly
        35                  40                  45

Pro Pro Gly Pro Pro Gly Pro Pro Gly Pro Pro Gly Pro Pro Gly Pro
    50                  55                  60

Pro Gly Pro Pro Gly Pro Pro Gly Pro Pro Gly Pro Pro Gly Pro Pro
65                  70                  75                  80

Gly Pro Pro Gly Pro Pro Gly Pro Pro Gly Pro Pro Gly Pro Pro Gly
            85                  90                  95
```

```
Pro Pro Gly Pro Pro Gly Pro Pro Gly Pro Pro Gly Pro
            100                 105                 110

Pro Gly Pro Gly Pro Gly Pro Gly Pro Gly Pro Pro
        115                 120                 125

Gly Pro Pro Gly Pro Pro Gly
    130                 135

<210> SEQ ID NO 17
<211> LENGTH: 9
<212> TYPE: PRT
<213> ORGANISM: Artificial Sequence
<220> FEATURE:
<223> OTHER INFORMATION: synthetic
<220> FEATURE:
<221> NAME/KEY: REPEAT
<222> LOCATION: (1)..(3)
<223> OTHER INFORMATION: the number of repeats of the string of residues
      1-3 is zero or any positive integer
<220> FEATURE:
<221> NAME/KEY: X
<222> LOCATION: (1)..(1)
<223> OTHER INFORMATION: Xaa is any amino acid
<220> FEATURE:
<221> NAME/KEY: X
<222> LOCATION: (2)..(2)
<223> OTHER INFORMATION: Xaa is any amino acid
<220> FEATURE:
<221> NAME/KEY: X
<222> LOCATION: (4)..(4)
<223> OTHER INFORMATION: Xaa is homocysteine
<220> FEATURE:
<221> NAME/KEY: X
<222> LOCATION: (5)..(5)
<223> OTHER INFORMATION: Xaa is any amino acid, but is the same amino
      acid as residue 2
<220> FEATURE:
<221> NAME/KEY: X
<222> LOCATION: (7)..(7)
<223> OTHER INFORMATION: Xaa is any amino acid, but is the same amino
      acid as residue 1
<220> FEATURE:
<221> NAME/KEY: REPEAT
<222> LOCATION: (7)..(9)
<223> OTHER INFORMATION: the number of repeats of the string of residues
      7-9 is zero or any positive integer
<220> FEATURE:
<221> NAME/KEY: X
<222> LOCATION: (8)..(8)
<223> OTHER INFORMATION: Xaa is any amino acid, but is the same amino
      acid as residue 2

<400> SEQUENCE: 17

Xaa Xaa Gly Xaa Xaa Gly Xaa Xaa Gly
1               5

<210> SEQ ID NO 18
<211> LENGTH: 9
<212> TYPE: PRT
<213> ORGANISM: Artificial Sequence
<220> FEATURE:
<223> OTHER INFORMATION: synthetic
<220> FEATURE:
<221> NAME/KEY: REPEAT
<222> LOCATION: (1)..(3)
<223> OTHER INFORMATION: the number of repeats of the string of
      residues 1-3 is 0-16
<220> FEATURE:
<221> NAME/KEY: REPEAT
<222> LOCATION: (1)..(9)
<223> OTHER INFORMATION: the total number of repeats of the string of
      residues 1-3 and 7-9 is 0-16
<220> FEATURE:
<221> NAME/KEY: X
```

```
<222> LOCATION: (1)..(1)
<223> OTHER INFORMATION: Xaa is any amino acid
<220> FEATURE:
<221> NAME/KEY: X
<222> LOCATION: (2)..(2)
<223> OTHER INFORMATION: Xaa is any amino acid
<220> FEATURE:
<221> NAME/KEY: X
<222> LOCATION: (4)..(4)
<223> OTHER INFORMATION: Xaa is homocysteine
<220> FEATURE:
<221> NAME/KEY: X
<222> LOCATION: (5)..(5)
<223> OTHER INFORMATION: Xaa is any amino acid, but is the same amino
      acid as residue 2
<220> FEATURE:
<221> NAME/KEY: REPEAT
<222> LOCATION: (7)..(9)
<223> OTHER INFORMATION: the number of repeats of the string of
      residues 7-9 is 0-16
<220> FEATURE:
<221> NAME/KEY: X
<222> LOCATION: (7)..(7)
<223> OTHER INFORMATION: Xaa is any amino acid, but is the same amino
      acid as residue 1
<220> FEATURE:
<221> NAME/KEY: X
<222> LOCATION: (8)..(8)
<223> OTHER INFORMATION: Xaa is any amino acid, but is the same amino
      acid as residue 2

<400> SEQUENCE: 18

Xaa Xaa Gly Xaa Xaa Gly Xaa Xaa Gly
1               5

<210> SEQ ID NO 19
<211> LENGTH: 9
<212> TYPE: PRT
<213> ORGANISM: Artificial Sequence
<220> FEATURE:
<223> OTHER INFORMATION: synthetic
<220> FEATURE:
<221> NAME/KEY: REPEAT
<222> LOCATION: (1)..(3)
<223> OTHER INFORMATION: the number of repeats of the string of residues
      1-3 is zero or any positive integer
<220> FEATURE:
<221> NAME/KEY: X
<222> LOCATION: (1)..(1)
<223> OTHER INFORMATION: Xaa is any amino acid
<220> FEATURE:
<221> NAME/KEY: X
<222> LOCATION: (2)..(2)
<223> OTHER INFORMATION: Xaa is any amino acid
<220> FEATURE:
<221> NAME/KEY: X
<222> LOCATION: (4)..(4)
<223> OTHER INFORMATION: Xaa is any amino acid, but si the same as amino
      acid as residue 1
<220> FEATURE:
<221> NAME/KEY: REPEAT
<222> LOCATION: (7)..(9)
<223> OTHER INFORMATION: the number of repeats of the string of residues
      7-9 is zero or any positive integer
<220> FEATURE:
<221> NAME/KEY: X
<222> LOCATION: (7)..(7)
<223> OTHER INFORMATION: Xaa is any amino acid, but si the same as amino
      acid as residue 1
<220> FEATURE:
<221> NAME/KEY: X
<222> LOCATION: (8)..(8)
<223> OTHER INFORMATION: Xaa is any amino acid, but si the same as amino
      acid as residue 2

<400> SEQUENCE: 19
```

```
Xaa Xaa Gly Xaa Cys Gly Xaa Xaa Gly
1               5

<210> SEQ ID NO 20
<211> LENGTH: 9
<212> TYPE: PRT
<213> ORGANISM: Artificial Sequence
<220> FEATURE:
<223> OTHER INFORMATION: synthetic
<220> FEATURE:
<221> NAME/KEY: REPEAT
<222> LOCATION: (1)..(3)
<223> OTHER INFORMATION: the number of repeats of the string of
      residues 1-3 is 0-16
<220> FEATURE:
<221> NAME/KEY: REPEAT
<222> LOCATION: (1)..(9)
<223> OTHER INFORMATION: the total number of repeats of the string of
      residues 1-3 and 7-9 is 0-16
<220> FEATURE:
<221> NAME/KEY: X
<222> LOCATION: (1)..(1)
<223> OTHER INFORMATION: Xaa is any amino acid
<220> FEATURE:
<221> NAME/KEY: X
<222> LOCATION: (2)..(2)
<223> OTHER INFORMATION: Xaa is any amino acid
<220> FEATURE:
<221> NAME/KEY: X
<222> LOCATION: (4)..(4)
<223> OTHER INFORMATION: Xaa is any amino acid, but is the same amino
      acid as residue 1
<220> FEATURE:
<221> NAME/KEY: REPEAT
<222> LOCATION: (7)..(9)
<223> OTHER INFORMATION: the number of repeats of the string of
      residues 7-9 is 0-16
<220> FEATURE:
<221> NAME/KEY: X
<222> LOCATION: (7)..(7)
<223> OTHER INFORMATION: Xaa is any amino acid, but is the same amino
      acid as residue 1
<220> FEATURE:
<221> NAME/KEY: X
<222> LOCATION: (8)..(8)
<223> OTHER INFORMATION: Xaa is any amino acid, but is the same amino
      acid as residue 2

<400> SEQUENCE: 20

Xaa Xaa Gly Xaa Cys Gly Xaa Xaa Gly
1               5

<210> SEQ ID NO 21
<211> LENGTH: 15
<212> TYPE: PRT
<213> ORGANISM: Artificial Sequence
<220> FEATURE:
<223> OTHER INFORMATION: synthetic
<220> FEATURE:
<221> NAME/KEY: X
<222> LOCATION: (1)..(1)
<223> OTHER INFORMATION: Xaa is any amino acid
<220> FEATURE:
<221> NAME/KEY: REPEAT
<222> LOCATION: (1)..(3)
<223> OTHER INFORMATION: the number of repeats of the string of residues
      1-3 is zero or any positive integer
<220> FEATURE:
<221> NAME/KEY: X
<222> LOCATION: (2)..(2)
<223> OTHER INFORMATION: Xaa is any amino acid
<220> FEATURE:
<221> NAME/KEY: X
<222> LOCATION: (4)..(4)
<223> OTHER INFORMATION: Xaa is any amino acid, but is the same amino
      acid as residue 1
```

```
<220> FEATURE:
<221> NAME/KEY: X
<222> LOCATION: (7)..(7)
<223> OTHER INFORMATION: Xaa is any amino acid, but is the same amino
      acid as residue 1
<220> FEATURE:
<221> NAME/KEY: REPEAT
<222> LOCATION: (7)..(9)
<223> OTHER INFORMATION: the number of repeats of the string of residues
      7-9 is zero or any positive integer
<220> FEATURE:
<221> NAME/KEY: X
<222> LOCATION: (8)..(8)
<223> OTHER INFORMATION: Xaa is any amino acid, but is the same amino
      acid as residue 2
<220> FEATURE:
<221> NAME/KEY: X
<222> LOCATION: (10)..(10)
<223> OTHER INFORMATION: Xaa is homocysteine
<220> FEATURE:
<221> NAME/KEY: X
<222> LOCATION: (11)..(11)
<223> OTHER INFORMATION: Xaa is any amino acid, but is the same amino
      acid as residue 2
<220> FEATURE:
<221> NAME/KEY: X
<222> LOCATION: (13)..(13)
<223> OTHER INFORMATION: Xaa is any amino acid, but is the same amino
      acid as residue 1
<220> FEATURE:
<221> NAME/KEY: REPEAT
<222> LOCATION: (13)..(15)
<223> OTHER INFORMATION: the number of repeats of the string of residues
      13-15 is zero or any positive integer
<220> FEATURE:
<221> NAME/KEY: X
<222> LOCATION: (14)..(14)
<223> OTHER INFORMATION: Xaa is any amino acid, but is the same amino
      acid as residue 2

<400> SEQUENCE: 21

Xaa Xaa Gly Xaa Cys Gly Xaa Xaa Gly Xaa Xaa Gly Xaa Xaa Gly
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: synthetic
<220> FEATURE:
<221> NAME/KEY: X
<222> LOCATION: (1)..(1)
<223> OTHER INFORMATION: Xaa is any amino acid
<220> FEATURE:
<221> NAME/KEY: REPEAT
<222> LOCATION: (1)..(3)
<223> OTHER INFORMATION: the number of repeats of the string of residues
      1-3 is zero or any positive integer
<220> FEATURE:
<221> NAME/KEY: X
<222> LOCATION: (2)..(2)
<223> OTHER INFORMATION: Xaa is any amino acid
<220> FEATURE:
<221> NAME/KEY: X
<222> LOCATION: (4)..(4)
<223> OTHER INFORMATION: Xaa is homocysteine
<220> FEATURE:
<221> NAME/KEY: X
<222> LOCATION: (5)..(5)
<223> OTHER INFORMATION: Xaa is any amino acid, but is the same amino
      acid as residue 2
<220> FEATURE:
<221> NAME/KEY: X
<222> LOCATION: (7)..(7)
<223> OTHER INFORMATION: Xaa is any amino acid, but is the same amino
      acid as residue 1
```

```
<220> FEATURE:
<221> NAME/KEY: REPEAT
<222> LOCATION: (7)..(9)
<223> OTHER INFORMATION: the number of repeats of the string of residues
      7-9 is zero or any positive integer
<220> FEATURE:
<221> NAME/KEY: X
<222> LOCATION: (8)..(8)
<223> OTHER INFORMATION: Xaa is any amino acid, but is the same amino
      acid as residue 2
<220> FEATURE:
<221> NAME/KEY: X
<222> LOCATION: (10)..(10)
<223> OTHER INFORMATION: Xaa is any amino acid, but is the same amino
      acid as residue 1
<220> FEATURE:
<221> NAME/KEY: X
<222> LOCATION: (13)..(13)
<223> OTHER INFORMATION: Xaa is any amino acid, but is the same amino
      acid as residue 1
<220> FEATURE:
<221> NAME/KEY: REPEAT
<222> LOCATION: (13)..(15)
<223> OTHER INFORMATION: the number of repeats of the string of residues
      13-15 is zero or any positive integer
<220> FEATURE:
<221> NAME/KEY: X
<222> LOCATION: (14)..(14)
<223> OTHER INFORMATION: Xaa is any amino acid, but is the same amino
      acid as residue 2

<400> SEQUENCE: 22

Xaa Xaa Gly Xaa Xaa Gly Xaa Xaa Gly Xaa Cys Gly Xaa Xaa Gly
1               5                   10                  15

<210> SEQ ID NO 23
<211> LENGTH: 9
<212> TYPE: PRT
<213> ORGANISM: Artificial Sequence
<220> FEATURE:
<223> OTHER INFORMATION: synthetic
<220> FEATURE:
<221> NAME/KEY: X
<222> LOCATION: (1)..(1)
<223> OTHER INFORMATION: Xaa is any amino acid
<220> FEATURE:
<221> NAME/KEY: REPEAT
<222> LOCATION: (1)..(3)
<223> OTHER INFORMATION: the number of repeats of the string of residues
      1-3 is zero or any positive integer
<220> FEATURE:
<221> NAME/KEY: X
<222> LOCATION: (2)..(2)
<223> OTHER INFORMATION: Xaa is any amino acid
<220> FEATURE:
<221> NAME/KEY: X
<222> LOCATION: (4)..(4)
<223> OTHER INFORMATION: Xaa is any amino acid, but is the same amino
      acid as residue 1
<220> FEATURE:
<221> NAME/KEY: X
<222> LOCATION: (7)..(7)
<223> OTHER INFORMATION: Xaa is any amino acid, but is the same amino
      acid as residue 1
<220> FEATURE:
<221> NAME/KEY: REPEAT
<222> LOCATION: (7)..(9)
<223> OTHER INFORMATION: the number of repeats of the string of residues
      7-9 is zero or any positive integer
<220> FEATURE:
<221> NAME/KEY: X
<222> LOCATION: (8)..(8)
<223> OTHER INFORMATION: Xaa is any amino acid, but is the same amino
      acid as residue 2

<400> SEQUENCE: 23
```

```
Xaa Xaa Gly Xaa Cys Gly Xaa Xaa Gly
1               5
```

<210> SEQ ID NO 24
<211> LENGTH: 9
<212> TYPE: PRT
<213> ORGANISM: Artificial Sequence
<220> FEATURE:
<223> OTHER INFORMATION: synthetic
<220> FEATURE:
<221> NAME/KEY: X
<222> LOCATION: (1)..(1)
<223> OTHER INFORMATION: Xaa is any amino acid
<220> FEATURE:
<221> NAME/KEY: REPEAT
<222> LOCATION: (1)..(3)
<223> OTHER INFORMATION: the number of repeats of the string of residues
      1-3 is zero or any positive integer
<220> FEATURE:
<221> NAME/KEY: X
<222> LOCATION: (2)..(2)
<223> OTHER INFORMATION: Xaa is any amino acid
<220> FEATURE:
<221> NAME/KEY: X
<222> LOCATION: (5)..(5)
<223> OTHER INFORMATION: Xaa is any amino acid, but is the same amino
      acid as residue 2
<220> FEATURE:
<221> NAME/KEY: X
<222> LOCATION: (7)..(7)
<223> OTHER INFORMATION: Xaa is any amino acid, but is the same amino
      acid as residue 1
<220> FEATURE:
<221> NAME/KEY: REPEAT
<222> LOCATION: (7)..(9)
<223> OTHER INFORMATION: the number of repeats of the string of residues
      7-9 is zero or any positive integer
<220> FEATURE:
<221> NAME/KEY: X
<222> LOCATION: (8)..(8)
<223> OTHER INFORMATION: Xaa is any amino acid, but is the same amino
      acid as residue 2

<400> SEQUENCE: 24

```
Xaa Xaa Gly Cys Xaa Gly Xaa Xaa Gly
1               5
```

OPTIMAL INTERSTRAND BRIDGE FOR COLLAGEN MIMICS

CROSS-REFERENCE TO RELATED APPLICATIONS

This application claims the benefit of U.S. provisional Application No. 62/049,550 filed on Sep. 12, 2014, which is incorporated by reference herein in its entirety.

STATEMENT REGARDING FEDERALLY SPONSORED RESEARCH OR DEVELOPMENT

This invention was made with government support under AR044276 awarded by the National Institutes of Health. The government has certain rights in the invention.

BACKGROUND

Collagen is the most abundant protein in vertebrates, occurring in virtually every tissue, including skin, tendon, bone, blood vessel, cartilage, ligament, and teeth. Collagen serves as the fundamental structural protein for vertebrate tissues. Collagen abnormalities are associated with a wide variety of human diseases, including arthritis, rheumatism, brittle bones, atherosclerosis, cirrhosis, and eye cataracts. Collagen is also critically important in wound healing.

Collagen is a fibrous protein consisting of three polypeptide chains that fold into a triple helix (Jenkins & Raines, *Nat. Prod. Rep.*, 19:49-59 (2002)). Mammals produce at least 46 distinct polypeptide chains that combine to form at least 28 distinct collagen types (Shoulders and Raines, *Annu. Rev. Biochem.* 2009. 78:929-58). In each of these variants, the polypeptide chains of collagen are composed of approximately 300 repeats of the tripeptide sequence Xaa-Yaa-Gly, where Xaa is often (but not always) a proline (Pro) residue and Yaa is often (but not always) a 4(R)-hydroxyproline (Hyp) residue, and Gly is always glycine. In connective tissue (such as bone, tendon, cartilage, ligament, skin, blood vessels, and teeth), individual collagen molecules are wound together in tight triple helices. These helices are organized into fibrils of great tensile strength (Jones & Miller, *J. Mol. Biol.*, 218:209-219 (1991)). Varying the arrangements and cross linking of the collagen fibrils enables vertebrates to support stress in one-dimension (e.g., tendons), two-dimensions (e.g., skin), or three-dimensions (e.g., cartilage).

Collagen's biological significance has made collagen a common target for biomaterials engineering, encouraging the development of self-assembling synthetic peptide systems that mimic the triple-helical architecture of collagen. At the core of such synthetic peptide systems are collagen-mimetic peptides, or CMPs. Although many of these efforts employ non-covalent means to program strand association, the covalent cross-linking of strands remains the most robust strategy (see, e.g., Kinberger, G. A.; Cai, W. B.; Goodman, M. *J. Am. Chem. Soc.* 2002, 124, 15162-15163; Barth, D.; Kyrieleis, O.; Frank, S.; Renner, C.; Moroder, L. *Chem.-Eur. J.* 2003, 9, 3703-3714; Homg, J.-C.; Hawk, A. J.; Zhao, Q.; Benedict, E. S.; Burke, S. D.; Raines, R. T. *Org. Lett.* 2006, 8, 4735-4738; Khew, S. T.; Tong, Y. W. *Biochemistry* 2008, 47, 585-596). Indeed, cystine "knots"—complex arrangements of interstrand Cys-Cys disulfide bridges—are found in natural fibrillar and fibril-associated collagens, inspiring the use of Cys-Cys bridges in synthetic collagen-like fibrillar assemblies that extend through sticky ends (see, e.g., Koide, T.; Homma, D. L.; Asada, S.; Kitagawa, K. *Bioorg. Med. Chem. Let.* 2005, 15, 5230-5233; Kotch, F. W.; Raines, R. T. *Proc. Natl. Acad. Sci. USA* 2006, 103, 3028-3033; Yamazaki, C. M.; Asada, S.; Kitagawa, K.; Koide, T. *Biopolymers* 2008, 90, 816-823; Yamazaki, C. M.; Kadoya, Y.; Hozumi, Okano-Kosugi, H.; Asada, S.; Kitagawa, K.; Nomizu, M.; Koide, T. *Biomaterials* 2010, 31, 1925-1934).

Collagen strands associate into triple helices with a single-residue stagger that gives rise to registers with an Xaa, Yaa, and Gly residue from each strand appearing at every cross-sectional plane along the triple helix, enabling cystine residues to be installed at proximal Xaa . . . Yaa pairs (FIG. 1A). However, an examination of neighboring Xaa . . . Yaa pairs in a $[(PPG)_{10}]_3$ crystal structure (PDB entry 1kf6) (Berisio, R.; Vitagliano, L.; Mazzarella, L.; Zagari, A. *Protein Sci.* 2002, 11, 262-270) reveals the Xaa . . . Yaa $C^\beta$ . . . $C^\beta$ distance (5 Å) to be longer than the average $C^\beta$ . . . $C^\beta$ distance (4 Å) predicted for a cystine dipeptide (Ozhogina, O. A.; Bominaar, E. L. *J Struct. Biol.* 2009, 168, 223-233). Thus, even neighboring Xaa and Yaa positions do not allow a geometry favorable for disulfide-bond formation, and any disulfide Xaa . . . Yaa cystine bonds formed between cysteine residues on separate CMP strands would exert unfavorable strain on the triple collagen triple helix.

Consistent with this observation, natural cystine knots are known to interrupt the triple-helical structure of collagen (see Barth, D.; Kyrieleis, O.; Frank, S.; Renner, C.; Moroder, L. *Chem.-Eur. J.* 2003, 9, 3703-3714 Boudko, S. P.; Engel, J.; Okuyama, K.; Mizuno, K.; Bachinger, H. P.; Schumacher, M. A. *J. Biol. Chem.* 2008, 283, 32580-32589; Wegener, H.; Paulsen, H.; Seeger, K. *J. Biol. Chem.* 2014, 289, 4861-4869). However, any effect of this disruption on collagen function is compensated by the length of common native collagen strands, which have about $10^3$ amino acid residues. In contrast, CMPs in typical synthetic assemblies are only about 30 amino acid residues long, and thus are more susceptible to the adverse impact from the strain of a interstrand cystine (cysteine-cysteine) disulfide linkage on the collagen-like triple helix.

Accordingly, there is a need in the art for compositions and methods for optimizing covalent interstrand bridges in collagen-mimetic peptides and other synthetic collagen-like biomaterials by reducing the strain associated with conventional cystine (cysteine-cysteine or Cys-Cys) disulfide linkages.

SUMMARY OF THE INVENTION

A cystine (Cys-Cys) disulfide bridge is a linkage that has been installed between collagen-mimetic peptide strands to help assemble collagen-like triple helices. However, Cys-Cys disulfide formation leads to a strained bridge which disrupts the resulting collagen-like triple helix.

Here, we disclose an improved disulfide linkage between collagen-mimetic peptide strands, a disulfide covalent bond between a homocysteine (one carbon longer than cysteine) in the canonical Xaa position of a first collagen-mimetic peptide strand and a cysteine in the canonical Yaa position of a second collagen-mimetic peptide strand. In the structure shown below, $R_1$, $R_2$, $R_3$, and $R_4$ represent the rest of the peptide chain.

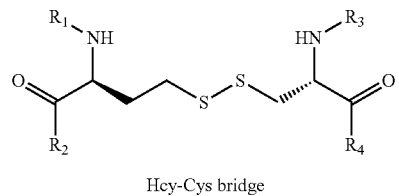

Hcy-Cys bridge

In silico screening of all possible linkages identified the disulfide bridge between proximal homocysteine (Hcy) and cysteine (Cys) as conferring much greater stability than a Cys-Cys bridge, but only when Hcy is installed in the Xaa position of the canonical Xaa-Yaa-Gly repeat and Cys is installed in the Yaa position. Thus, a Hcy-Cys bridge is markedly superior to a Cys-Hcy bridge. We synthesized all of the 1,2 combinations and found that collagen mimetic peptides (CMPs) validate this design. Only Hcy-Cys bridges improved triple-helical structure and stability upon disulfide-bond formation. Thus, this specific linker design will enhance CMP-based biomaterials and enable previously inaccessible molecular designs.

Accordingly, in a first aspect, the disclosure encompasses a collagen-mimetic peptide comprising the formula (Xaa-Yaa-Gly)$_n$-Hcy-Yaa-Gly-(Xaa-Yaa-Gly)$_m$ (SEQ ID NO:17), wherein Gly is glycine, Hcy is homocysteine, each Xaa and each Yaa is independently any amino acid residue, n is zero or any positive integer, and m is zero or any positive integer. The core amino acid sequence encompassed by this general formula, (Xaa-Yaa-Gly)-Hcy-Yaa-Gly-(Xaa-Yaa-Gly), is SEQ ID NO:1.

In some embodiments, each Xaa and each Yaa is independently selected from the group consisting of proline, hydroxyproline, and an amino acid residue having a side chain capable of being functionalized. Amino acid residues having a side chain capable of being functionalized may include, as non-limiting examples, an amine, an alkene, an aldehyde, an alkyne, an azide, or a thiol. One specific non-limiting example of such an amino acid residue is lysine.

In some embodiments, each Xaa is proline and each Yaa is hydroxyproline or proline. In some embodiments, at least one Xaa or Yaa is an amino acid residue having a side chain capable of being functionalized, and this amino acid residue is attached to a cargo moiety, such as a therapeutic agent or a detection agent.

In some embodiments, n is an integer from 0 to 16, m is an integer from 0 to 16, and the sum of n+m is from 0 to 16.

In some embodiments, the collagen-mimetic peptide consists essentially of the formula (Xaa-Yaa-Gly)$_n$-Hcy-Yaa-Gly-(Xaa-Yaa-Gly)$_m$ (SEQ ID NO:18), wherein Gly is glycine, Hcy is homocysteine, each Xaa and each Yaa is independently any amino acid residue, n is an integer from 0 to 16, m is an integer from 0 to 16, and the sum of n+m is from 0 to 16.

In a second aspect, the disclosure encompasses a multi-stranded collagen-mimetic peptide comprising (a) a first strand comprising the formula (Xaa-Yaa-Gly)$_n$-Hcy-Yaa-Gly-(Xaa-Yaa-Gly)$_m$ (SEQ ID NO:17), wherein Gly is glycine, Hcy is homocysteine, each Xaa and each Yaa is independently any amino acid residue, n is zero or any positive integer, and m is zero or any positive integer; and (b) a second strand comprising the formula (Xaa-Yaa-Gly)$_p$-Xaa-Cys-Gly-(Xaa-Yaa-Gly)$_q$ (SEQ ID NO:19), wherein Gly is glycine, Cys is cysteine, each Xaa and each Yaa is independently any amino acid residue, p is zero or any positive integer, and q is zero or any positive integer. The core amino acid sequence encompassed by this general formula, (Xaa-Yaa-Gly)-Xaa-Cys-Gly-(Xaa-Yaa-Gly), is SEQ ID NO:2. The first and second strands are covalently bonded with a disulfide bond between the sulfur atom of the thiol side chain of the homocysteine residue of the first strand and the sulfur atom of the thiol side chain of the cysteine residue of the second strand.

In some embodiments, each Xaa and each Yaa is independently selected from the group consisting of proline, hydroxyproline, and an amino acid residue having a side chain capable of being functionalized. In some non-limiting embodiments, the amino acid residue having a side chain capable of being functionalized is lysine.

In some embodiments, each Xaa is proline and each Yaa is hydroxyproline or proline. In some embodiments, at least one Xaa or Yaa is an amino acid residue having a side chain capable of being functionalized, and this amino acid residue is attached to a cargo moiety, such as a therapeutic agent or a detection agent.

In some embodiments, n is an integer from 0 to 16, m is an integer from 0 to 16, the sum of n+m is from 0 to 16, p is an integer from 0 to 16, q is an integer from 0 to 16, and the sum of p+q is from 0 to 16.

In some embodiments, the first strand consists essentially of the formula (Xaa-Yaa-Gly)$_n$-Hcy-Yaa-Gly-(Xaa-Yaa-Gly)$_m$ (SEQ ID NO:18), wherein Gly is glycine, Hcy is homocysteine, each Xaa and each Yaa is independently any amino acid residue, n is an integer from 0 to 16, m is an integer from 0 to 16, and the sum of n+m is from 0 to 16; and the second strand consists essentially of the formula (Xaa-Yaa-Gly)$_p$-Xaa-Cys-Gly-(Xaa-Yaa-Gly)$_q$ (SEQ ID NO:20), wherein Gly is glycine, Cys is cysteine, each Xaa and each Yaa is independently any amino acid residue, p is an integer from 0 to 16, q is an integer from 0 to 16, and the sum of p+q is from 0 to 16.

In some embodiments, the multi-stranded collagen-mimetic peptide consists essentially of the first strand and the second strand joined with a covalent disulfide bond, as described above.

In some embodiments, the second strand comprises the formula (Xaa-Yaa-Gly)$_p$-Xaa-Cys-Gly-(Xaa-Yaa-Gly)$_q$-Hcy-Yaa-Gly-(Xaa-Yaa-Gly)$_r$ (SEQ ID NO:21) (the core sequence (Xaa-Yaa-Gly)-Xaa-Cys-Gly-(Xaa-Yaa-Gly)-Hcy-Yaa-Gly-(Xaa-Yaa-Gly) is SEQ ID NO:3) or (Xaa-Yaa-Gly)$_p$-Hcy-Yaa-Gly-(Xaa-Yaa-Gly)$_q$-Xaa-Cys-Gly-(Xaa-Yaa-Gly)$_r$ (SEQ ID NO:22) (the core sequence (Xaa-Yaa-Gly)-Hcy-Yaa-Gly-(Xaa-Yaa-Gly)-Xaa-Cys-Gly-(Xaa-Yaa-Gly) is SEQ ID NO:4), wherein Gly is glycine, Cys is cysteine, each Xaa and each Yaa is independently any amino acid residue, and p, q and r are independently zero or any positive integer. In some such embodiments, the multi-stranded collagen-mimetic peptide further includes a third strand comprising the formula (Xaa-Yaa-Gly)$_j$-Xaa-Cys-Gly-(Xaa-Yaa-Gly)$_k$ (SEQ ID NO:23), wherein Gly is glycine, Cys is cysteine, each Xaa and each Yaa is independently any amino acid residue, and j and k are independently zero or any positive integer. The second and third strands are covalently bonded with a disulfide bond between the sulfur atom of the thiol side chain of the homocysteine residue of the second strand and the sulfur atom of the thiol side chain of the cysteine residue of the third strand. In some such embodiments, (n+m+1)=(p+q+r+2), (p+q+r+2)=(j+k+1), or both. In yet other such embodiments, one of the homocysteine residues is substituted with a cysteine residue, such that either the first and second or the second and third strands are covalently bonded with a Cys-Cys disulfide bond.

In a third aspect, the disclosure encompasses a synthetic collagen-like fibrillar assembly that includes a plurality of the multi-stranded collagen-mimetic peptides, as described above. Some such embodiments encompass a composition that includes the synthetic collagen-like fibrillar assembly and a therapeutic agent, such as a growth factor.

In a fourth aspect, the disclosure encompasses a kit that includes a plurality of the multi-stranded collagen-mimetic peptides described above. In some embodiments, the kit may further include a therapeutic agent, such as a growth factor.

In a fifth aspect, the disclosure encompasses a method of making a collagen-mimetic peptide. The method includes the step of substituting a non-homocysteine Xaa residue in a peptide comprising the formula (Xaa-Yaa-Gly)$_n$, wherein Gly is glycine, each Xaa and each Yaa is independently any amino acid residue, and n is zero or any positive integer, with a homocysteine residue. In some embodiments, the non-homocysteine Xaa residue that is substituted with homocysteine is a proline residue. In some embodiments, each unsubstituted Xaa and each Yaa is independently selected from the group consisting of proline, hydroxyproline, and an amino acid residue having a side chain capable of being functionalized. In some embodiments, each unsubstituted Xaa is proline and each Yaa is proline or hydroxyproline.

In a sixth aspect, the disclosure encompasses a method of making a multi-stranded collagen-mimetic peptide. The method includes the step of forming a covalent disulfide bond between a first strand comprising the formula (Xaa-Yaa-Gly)$_n$-Hcy-Yaa-Gly-(Xaa-Yaa-Gly)$_m$ (SEQ ID NO:17), wherein Gly is glycine, Hcy is homocysteine, each Xaa and each Yaa is independently any amino acid residue, n is zero or any positive integer, and m is zero or any positive integer; and a second strand comprising the formula (Xaa-Yaa-Gly)$_p$-Xaa-Cys-Gly-(Xaa-Yaa-Gly)$_q$ (SEQ ID NO: 19), wherein Gly is glycine, Cys is cysteine, each Xaa and each Yaa is independently any amino acid residue, p is zero or any positive integer, and q is zero or any positive integer. The covalent disulfide bond is formed between the sulfur atom of the thiol side chain of the homocysteine residue of the first strand and the sulfur atom of the thiol side chain of the cysteine residue of the second strand.

In some embodiments, each Xaa and each Yaa is independently selected from the group consisting of proline, hydroxyproline, and an amino acid residue that is capable of being functionalized. In some embodiments, each Xaa is proline and each Yaa is proline or hydroxyproline.

In some embodiments, the first strand consists essentially of the formula (Xaa-Yaa-Gly)$_n$-Hcy-Yaa-Gly-(Xaa-Yaa-Gly)$_m$ (SEQ ID NO:18), wherein Gly is glycine, Hcy is homocysteine, each Xaa and each Yaa is independently any amino acid residue, n is an integer from 0 to 16, m is an integer from 0 to 16, and the sum of n+m is from 0 to 16; and the second strand consists essentially of the formula (Xaa-Yaa-Gly)$_p$-Xaa-Cys-Gly-(Xaa-Yaa-Gly)$_q$ (SEQ ID NO:20), wherein Gly is glycine, Cys is cysteine, each Xaa and each Yaa is independently any amino acid residue, p is an integer from 0 to 16, q is an integer from 0 to 16, and the sum of p+q is from 0 to 16.

In some embodiments, the method further includes the step of forming a covalent disulfide bond between the sulfur atom of the thiol side chain of the homocysteine residue of the second strand and the sulfur atom of the thiol side chain of the cysteine residue of a third strand, wherein the third strand comprises the formula (Xaa-Yaa-Gly)$_j$-Xaa-Cys-Gly-(Xaa-Yaa-Gly)$_k$ (SEQ ID NO:23), wherein Gly is glycine, Cys is cysteine, each Xaa and each Yaa is independently any amino acid residue, and j and k are independently zero or any positive integer.

In a seventh aspect, the disclosure encompasses a method of making a synthetic collagen-like fibrillar assembly. The method includes the step of contacting a first multi-stranded collagen-mimetic peptide as described above with one or more second multi-stranded collagen-mimetic peptides as described above. The first and second multi-stranded collagen-mimetic peptides self-assemble into a larger synthetic collagen-like fibrillar assembly.

In an eighth aspect, the disclosure encompasses a method of facilitating wound healing. The method includes the step of contacting a wound with a composition that includes the multi-stranded collagen-mimetic peptide described above, or the synthetic collagen-like fibrillar assembly described above, thereby facilitating the healing of the wound. In some embodiments, the composition further includes a therapeutic agent, such as a growth factor.

In a ninth aspect, the disclosure encompasses the use of the collagen-mimetic peptide described above or the synthetic collagen-like fibrillar assembly described above to facilitate wound healing in a subject.

In a tenth aspect, the disclosure encompasses the use of the collagen-mimetic peptide described above, the multi-stranded collagen-mimetic peptide described above, or the synthetic collagen-like fibrillar assembly described above in the manufacture of a medicament to facilitate wound healing in a subject.

Other objects, advantages, and features of the present invention will become apparent upon review of the specification, drawings, and claims.

DESCRIPTION OF THE DRAWINGS

(FIG. 6A) Experimental (solid) and calculated $T_m$ values (dashed lines) for heterotrimers. (FIG. 6B) Experimental $T_m$ values for homotrimers. (FIG. 6C) Calculated strain energy, plotted as $-E_{strain}$ to ease comparisons with experimental data. (FIG. 6D) $[\theta]_{max}$ from CD spectra acquired at 4° C. Values for s2 are included in panels 6A, 6B, and 6D for comparison.

FIGS. 8A, 8B, 8C, 8D, 8E, 8F, 8G and 8H show circular dichroism spectra and melting profiles for linked-dimer—s2 mixtures and individual strands. Each panel displays data acquired on the same instrument: (FIG. 8A) CD spectra and (FIG. 8B) temperature melts for x–y·s2 featuring c-c and h-c linkers, (FIG. 8C) CD spectra and (FIG. 8D) temperature melts for x–y·s2 featuring c-h and h-h linkers, (FIG. 8E) CD spectra and (FIG. 8F) temperature melts for homotrimers of individual strands, and (FIG. 8G) CD spectra and (FIG. 8H) temperature melts for s1x+s2+s3y mixtures.

DETAILED DESCRIPTION

Figures 1A, 1B:
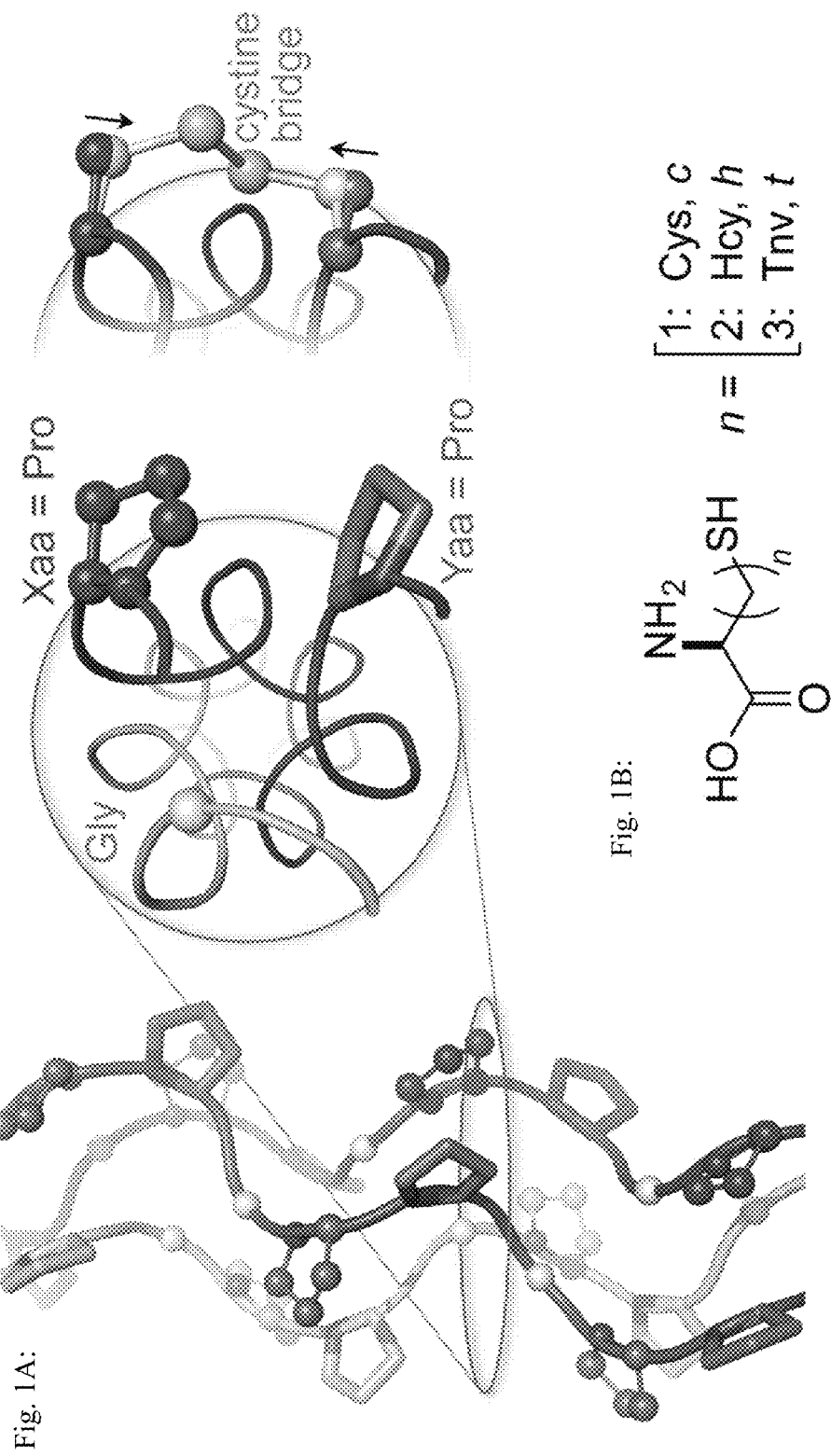
FIG. 1A shows side and cross-sectional views of (PPG)$_{10}$ (SEQ ID NO:6) trimer displaying Xaa (balls & sticks), Yaa (sticks) and Gly positions (white balls). Positioning of Xaa and Yaa residues are shown in a cross-section. Application of a cystine bridge here pulls $C^\beta$ atoms inward and away from their original positions (black arrows), indicating a strained linker.
FIG. 1B shows the structure of cysteine analogs considered in disulfide bridges in Example 1. All models were generated with PyMOL v1.3, unless noted otherwise.

We disclose herein an improved linkage between collagen-mimetic peptide strands: a disulfide covalent bond between a homocysteine in the canonical Xaa position of a first collagen-mimetic peptide strand and a cysteine in the canonical Yaa position of a second collagen-mimetic peptide strand.

In native collagen, the polyproline type II helices consist of over 300 repeats of the unit Xaa-Yaa-Gly. Although in native collagen, Xaa is often (2S)-proline (Pro) and the Yaa is often (2S,4R)-4-hydroxyproline (Hyp), any amino acid residue may occur at these positions. Accordingly, the Xaa and Yaa position residues of the disclosed collagen-mimetic peptides can be any amino acid. In some non-limiting embodiments, Xaa and Yaa are selected from proline, hydroxyproline, or lysine. For ease of synthesis, proline is sometimes used in both the Xaa and Yaa positions in collagen-mimetic peptide strands. The use of hydroxyproline in the Yaa position may improve the stability of the collagen-like triple helix. However, any other amino acid or amino acid derivatives may be used at the Xaa and Yaa positions, including without limitation those disclosed in U.S. Patent Publication No. 2007/0275897, which is incorporated by reference herein.

To improve functionality, the collagen-mimetic peptides may be functionalized with any desired moiety. As a non-limiting example, lysine may be included in the sequence of the collagen-mimetic peptides (CMPs) so that fluorophores, therapeutics or other cargo can be attached to the growing assembly at the $N^\varepsilon$ atom. However, Lys is not the only residue that could facilitate such attachment, and other side-chains could be used, as well. For example, side chains containing alkenes, alkynes, aldehydes, azides, and thiols could be all be used for this purpose.

Accordingly, any amino acid residue capable of being functionalized may be included at the Xaa or Yaa position to facilitate functionalizing the collagen-mimetic peptide. The amino side chain of lysine or any other amino acid residue capable of being functionalized may be functionalized with a desired moiety using standard synthetic techniques known in the art. The addition of the desired moiety on the amino side chain terminus can be done separately from the formation of the disulfide bridge formation, so that the assembly of the multi-stranded collagen-mimetic peptide is not affected. Alternatively, the disulfide bridge itself may be subsequently broken and functionalized at the terminal thiol, as desired, using methods known in the art.

The disclosed collagen-mimetic peptides, multi-stranded collagen-mimetic peptides, and synthetic collagen-like fibrillar assemblies have a variety of potential applications, including without limitation in biomaterials used for tissue repair and/or tissue engineering.

As a non-limiting example, the disclosed collagen-mimetic peptides may be used to treat wounded tissue or to facilitate the delivery of therapeutic agents or cytoactive factors to acute or chronic tissue wounds. Compositions containing collagen-mimetic peptides may be used for wound dressing, in dural closures, for reinforcement of compromised tissues, and in guided tissue regeneration. Such compositions can be used as vehicles for the sustained release of pharmaceuticals or therapeutic agents, including without limitation antibiotics or growth factors, such as recombinant human growth factor (hGF), platelet-derived growth factor (PDGF), fibroblast growth factor (FGF), or neuropeptides, such as Substance P.

Therapeutics, such as growth factors, can be attached to self-assembling linked-dimers to aid in wound healing. However, therapeutic delivery could also be realized with a similar system that does not self-assemble. Blunt-ended linked dimers, such as those disclosed in Examples 1 and 2 below, can be loaded with cargo, and administered to the wound site, in a manner similar to what is currently done with single strands. Thus, using a "plurality" of linked-dimers would not be necessary.

As another non-limiting example, the disclosed collagen-mimetic peptides may be used in cell culture scaffold compositions for both in vivo and in vitro applications.

Unless otherwise defined, all technical and scientific terms used herein have the same meaning as commonly understood by one of ordinary skill in the art to which this invention belongs. Although suitable methods and materials for the practice or testing of the present invention are described below, other methods and materials similar or equivalent to those described herein, which are well known in the art, can also be used.

The following Examples are offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

EXAMPLES

Example 1: Optimal Interstrand Bridges for Collagen-Like Biomaterials

In some natural collagen triple helices, cysteine (Cys) residues on neighboring strands are linked by disulfide bonds, enhancing association and maintaining proper register. Similarly, Cys-Cys disulfide bridges have been used to impose specific associations between collagen-mimetic peptides (CMPs). In this example, screening a library of disulfide linkers in silico for compatibility with collagen identified the disulfide bridge between proximal homocysteine (Hcy) and Cys as conferring much greater stability than a Cys-Cys bridge, but only when Hcy was installed in the Xaa position of the canonical Xaa-Yaa-Gly repeat and Cys was installed in the Yaa position. Experimental evaluation of CMPs that host alternative thiols validated this design: only Hcy-Cys bridges improved triple-helical stability upon disulfide-bond formation. This privileged linker can enhance CMP-based biomaterials and enable previously inaccessible molecular designs.

Introduction.

Cystine "knots"— complex arrangements of interstrand Cys-Cys disulfide bridges—are found in natural fibrillar and fibril-associated collagens, inspiring the use of Cys-Cys bridges in synthetic collagen-like fibrillar assemblies that extend through sticky ends. In this Example, we determined the effect of this natural disulfide bridge and synthetic alternatives on triple-helix stability.

The amino-acid sequence of natural collagen is defined by repeating (Xaa-Yaa-Gly) units that feature (2S)-proline (Pro) and (2S,4R)-4-hydroxyproline (Hyp) at the Xaa and Yaa positions, which favor the formation of polyproline-type II helices. Collagen strands associate into triple helices with a single-residue stagger that gives rise to registers with an Xaa, Yaa, and Gly residue from each strand appearing at every cross-sectional plane along the triple helix, enabling cystines to be installed at proximal Xaa . . . Yaa pairs (FIG. 1A).

An examination of neighboring Xaa . . . Yaa pairs in a $[(PPG)_{10}]_3$ crystal structure (PDB entry 1kf6)[9] ($(PPG)_{10}$ is SEQ ID NO:6) reveals the Xaa . . . Yaa $C^\beta$ . . . $C^\beta$ distance (5 Å) to be longer than the average $C^\beta$ . . . $C^\beta$ distance (4 Å) predicted for a cystine. Thus, even neighboring Xaa and Yaa positions might not allow a geometry favorable for disulfide-bond formation. Natural cystine knots interrupt triple-helical structure, but any effect on collagen function is compensated by the length of common collagen strands, which have about $10^3$ residues. In contrast, CMPs in typical synthetic assemblies are only ~30 residues long, and could be more susceptible to an adverse impact from the strain of a cystine linkage.

General Experimental Design, Results, and Discussion.

We reasoned that relieving strain within the disulfide bridge could be the key step toward an interstrand "staple" that conforms to the collagen triple helix. Toward this end, we used molecular modeling to explore longer linkers that employ combinations of cysteine (Cys) and the homologated analogs homocysteine (Hcy) and thionorvaline (Tnv), which have one, two, and three side-chain methylene groups, respectively (FIG. 1B). Neighboring Xaa and Yaa positions in the $[(PPG)_{10}]_3$ crystal structure_ ($(PPG)_{10}$ is SEQ ID NO:6) were replaced with Cys, Hcy, or Tnv. All nine possible Xaa-Yaa strand pairs were created in silico. After optimization, energies were evaluated (See Mayo, S. L.; Olafson, B. D.; Goddard, W. A., III, *J. Phys. Chem.* 1990, 94, 8897-8909; Lim, K. T.; Brunett, S.; Iotov, M.; McClurg, R. B.; Vaidehi, N.; Dasgupta, S.; Taylor, S.; Goddard, W. A., III, *J. Comput. Chem.* 1997, 18, 501-521) in a fixed triple-helical backbone, both before (Xaa . . . Yaa) and after (Xaa-Yaa) disulfide-bond formation. Linker strain is defined as $E_{strain}=E_{x-y}-E_{x\cdot y}$, which is the change in energy upon disulfide-bond formation. Disulfide-bridges are designated by a code that identifies the Xaa-Yaa pair: "c" for Cys, "h" for Hcy, and "t" for Tnv, such that "c-c" represents a cystine.

Figure 2:
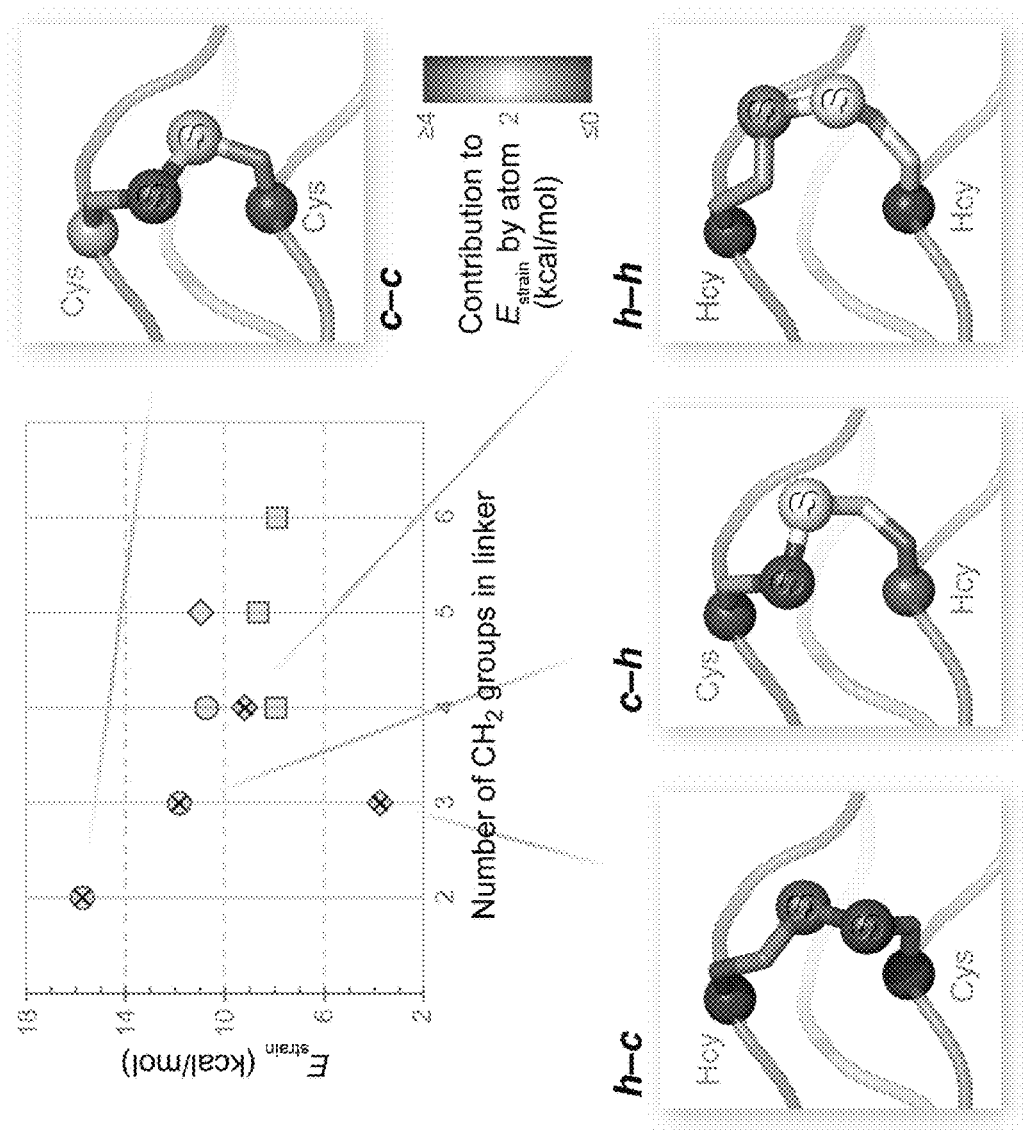
FIG. 2 shows computational design of disulfide bridges compatible with the collagen triple helix. Computed values of $E_{strain}$ for disulfides are plotted with respect to linker size. Linkers having Xaa=Cys, Hcy, and Tnv are represented by circles, diamonds, and squares, respectively. Designs selected for experimental evaluation are marked with an "x". Lines point to images of computational models in which $C^\alpha$ and S are shown as balls and shading represent the contribution of atoms to the value of $E_{strain}$.

Increasing linker length relieves the strain on the disulfide. The value of $E_{strain}$ is largest for the c-c bridge, which contains only two methylene groups (FIG. 2). When four or more methylene groups are present, bond and angle strain is eased substantially, and the value of $E_{strain}$ decreases by ~7 kcal/mol. Still, dihedral strain remains elevated due to eclipsed C—C or C—S torsion angles (See Table 1 and Table 2).

TABLE 1

Breakdown of $E_{strain}$ into Force-Field Energy Components:

| Linker type | CH$_2$ groups on linker, $n_{Xaa} + n_{Yaa}$ | $E_{strain}$ components (kcal/mol) | | | | |
|---|---|---|---|---|---|---|
| | | Total | Bonds | Angles | Torsions | Van der Waals |
| h-c | 3 | 3.8 | 0.2 | 0.7 | 2.3 | 0.6 |
| t-t | 6 | 7.9 | 0.2 | 1.6 | 2.6 | 3.5 |
| t-c | 4 | 8.0 | 0.4 | 1.2 | 2.5 | 3.9 |
| t-h | 5 | 8.7 | 0.3 | 1.2 | 5.6 | 1.7 |
| h-h | 4 | 9.2 | 0.2 | 1.2 | 5.8 | 2.0 |
| c-t | 4 | 10.7 | 0.3 | 1.6 | 6.7 | 2.3 |
| h-t | 5 | 11.0 | 0.5 | 1.9 | 5.0 | 3.6 |
| c-h | 3 | 11.9 | 0.6 | 4.1 | 5.3 | 1.9 |
| c-c | 2 | 15.9 | 1.2 | 9.1 | 4.5 | 1.2 |

TABLE 2

Side-chain[a] and Disulfide[b] Torsion Angles Along the Linker as Obtained from Computational Models Reported in Degrees:

| | c-c | h-c | c-h | h-h | c-t | h-t | t-t | t-h | t-c |
|---|---|---|---|---|---|---|---|---|---|
| Xaa | Cys | Hcy | Cys | Hcy | Cys | Hcy | Tnv | Tnv | Tnv |
| C$^\alpha$–C$^\beta$ | 42.5 | 49.8 | 42.2 | 65.6 | 53.8 | 43.1 | 81.9 | 49.2 | 68.1 |
| C$^\beta$–C$^\gamma$ | 81.1 | 73.8 | 112.5 | 102.8 | 113.2 | 160.1 | 159.4 | 152.4 | −175.4 |
| C$^\gamma$–C$^\delta$ | | −160.9 | | −168.3 | | −76.2 | −146.9 | −83.3 | −165.0 |
| C$^\delta$–S | | | | | | −69.7 | −90.1 | −60.5 | |
| S–S | −146.5 | 129.6 | −114.4 | 81.5 | −153.3 | −90.9 | 126.6 | 94.7 | 106.3 |
| S–C$^\delta$ | | | | | 60.7 | 92.9 | −87.5 | | |
| C$^\delta$–C$^\gamma$ | | −49.2 | | −123.7 | −104.3 | −113.9 | −62.0 | −122.9 | |
| C$^\gamma$–C$^\beta$ | 69.3 | −79.2 | 104.4 | 129.7 | 135.7 | 149.1 | 169.1 | 149.2 | −132.5 |
| C$^\beta$–C$^\alpha$ | −127.6 | −71.4 | −154.0 | −158.9 | −167.0 | −170.1 | −176.4 | −168.2 | −44.2 |
| Yaa | Cys | Cys | Hcy | Hcy | Tnv | Tnv | Tnv | Hcy | Cys |

[a]Side-chain torsion angles across C—C and C—S bonds that are closer to the eclipsed rather than the staggered conformation are shown in bold typeface.
[b]Torsion angles across the disulfide bond are underlined for each linker, and those angles closer to energy maxima (0° and 180°) rather than minima (±90°) are shown in bold typeface.

Interestingly, the h-c disulfide (Xaa=Hcy; Yaa=Cys) falls outside this trend and is free of strained torsions. Despite being among the shortest linkers in the set, h-c forms the most stable disulfide bridge: 12 kcal/mol lower in energy than c-c. The Xaa and Yaa positions are not related by symmetry, and the c-h bridge does not show the dramatic reduction in the value of $E_{strain}$ as does the h-c bridge.

Figures 3A, 3B:
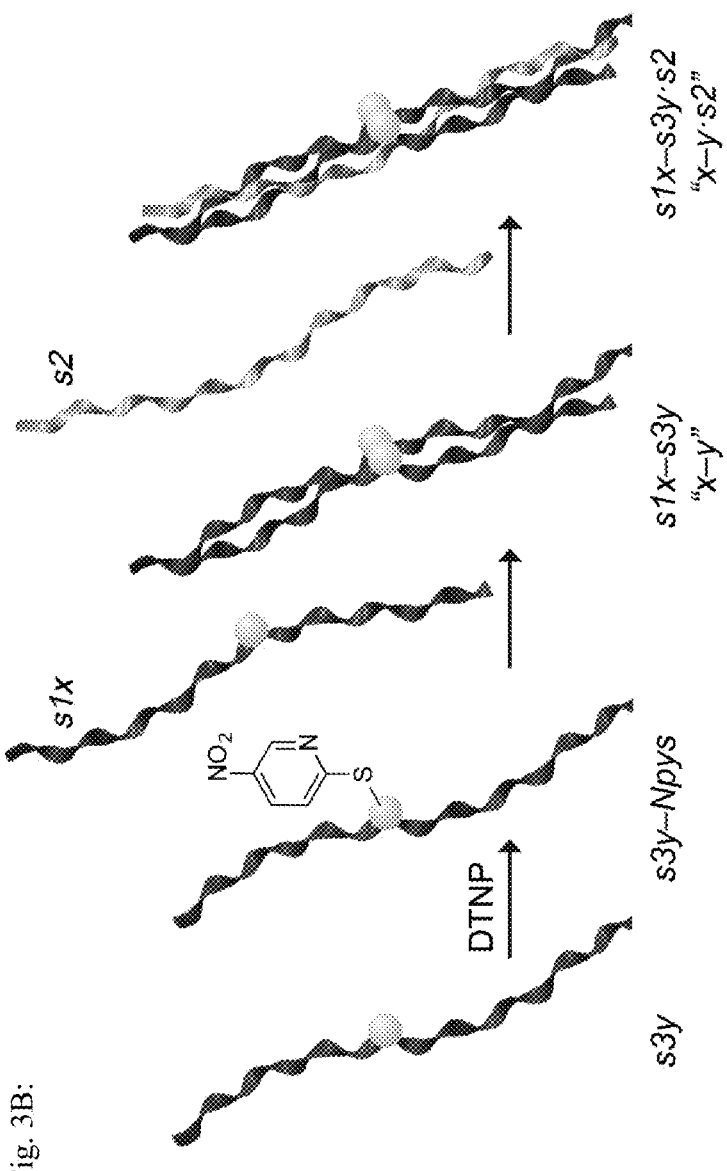
FIGS. 3A and 3B show design (FIG. 3A) and construction (FIG. 3B) of CMPs for experimental assessment of disulfide linkers. Ribbons were generated with VMD v1.9. s1x is SEQ ID NO:5; s2 is SEQ ID NO:6, and s3y is SEQ ID NO:7.

To validate our computational predictions, we synthesized CMPs poised to form a c-c, h-c, c-h, or h-h bridge. This set includes bridges predicted to be the best (h-c) and worst (c-c). The disulfide-linked [(PPG)$_{10}$]$_3$ variants were constructed and characterized using methods established previously (FIG. 3A) (see Rabanal, F.; DeGrado, W. F.; Dutton, P. L. *Tetrahedron Lett* 1996, 37, 1347-1350; Kotch, F. W.; Raines, R. T. *Proc. Natl. Acad. Sci. USA* 2006, 103, 3028-3033). Of the three strands, the leading strand hosts the Xaa partner of the disulfide through either a Pro16Cys (for s1c) or a Pro16Hcy (s1h) substitution, whereas the lagging strand bearing the Yaa partner has a Pro14Cys (s3c) or Pro14Hcy (s3h) substitution. After an interstrand disulfide-bond was formed by a thiol-disulfide interchange reaction (FIG. 3B), a third, wild-type strand (s2) was introduced to associate with the disulfide-bonded pair and thereby complete the triple-helix. The placement of the linker between leading and lagging strands forces s2 to occupy the middle register, avoiding degenerate structures. The thermal stability and the oligomerization state of triple helices formed by association of s1x-s3y (x-y) pairs and s2 were assessed with circular dichroism (CD) spectroscopy and analytical ultracentrifugation (AUC).

Figures 4A, 4B:
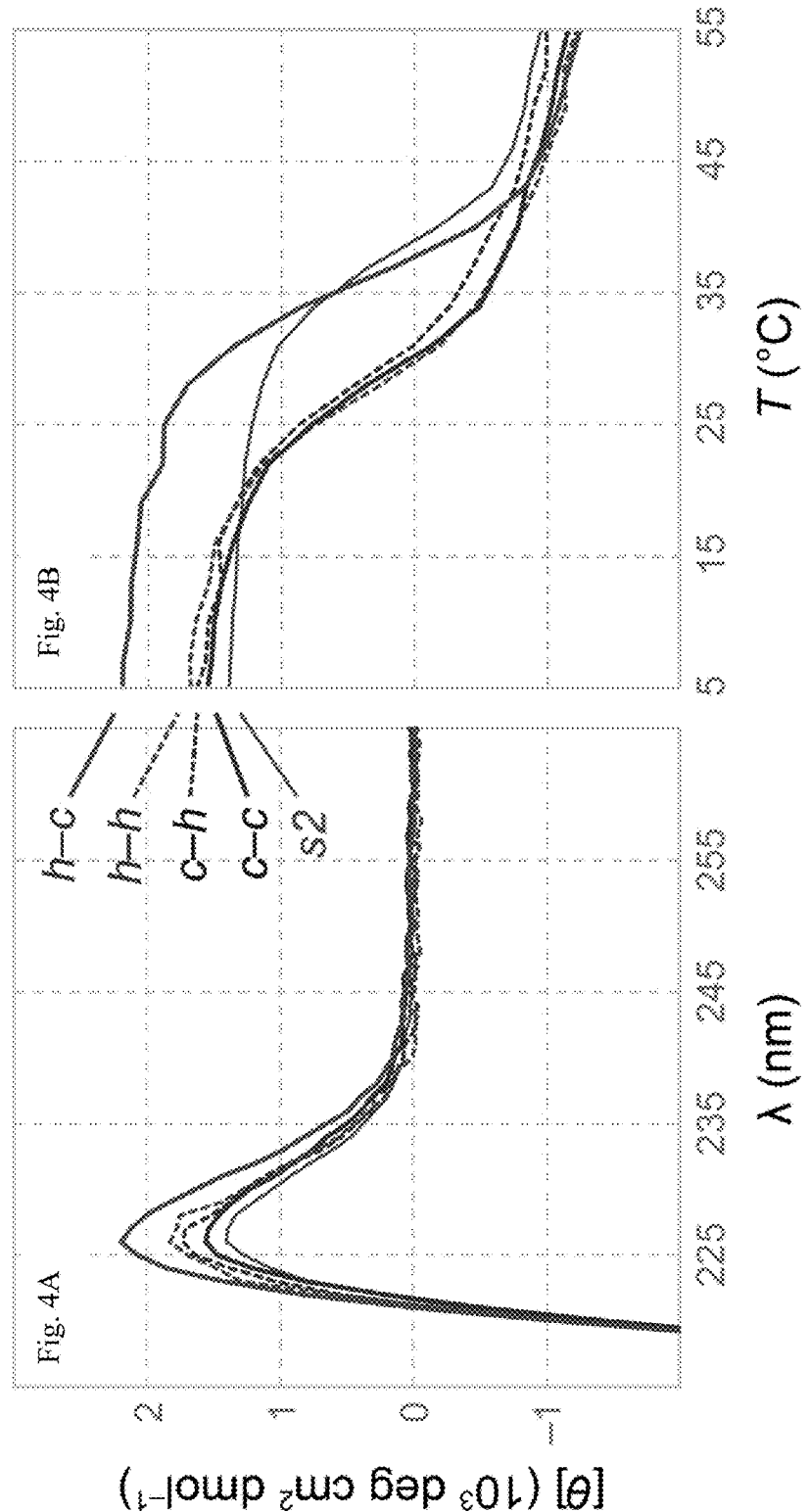
FIGS. 4A and 4B show CD spectra (FIG. 4A) and thermal denaturation data (FIG. 4B) for (PPG)$_{10}$ (SEQ ID NO:6) and x–y·s2 triple helices. For spectra without smoothing, see.
Figure 5:
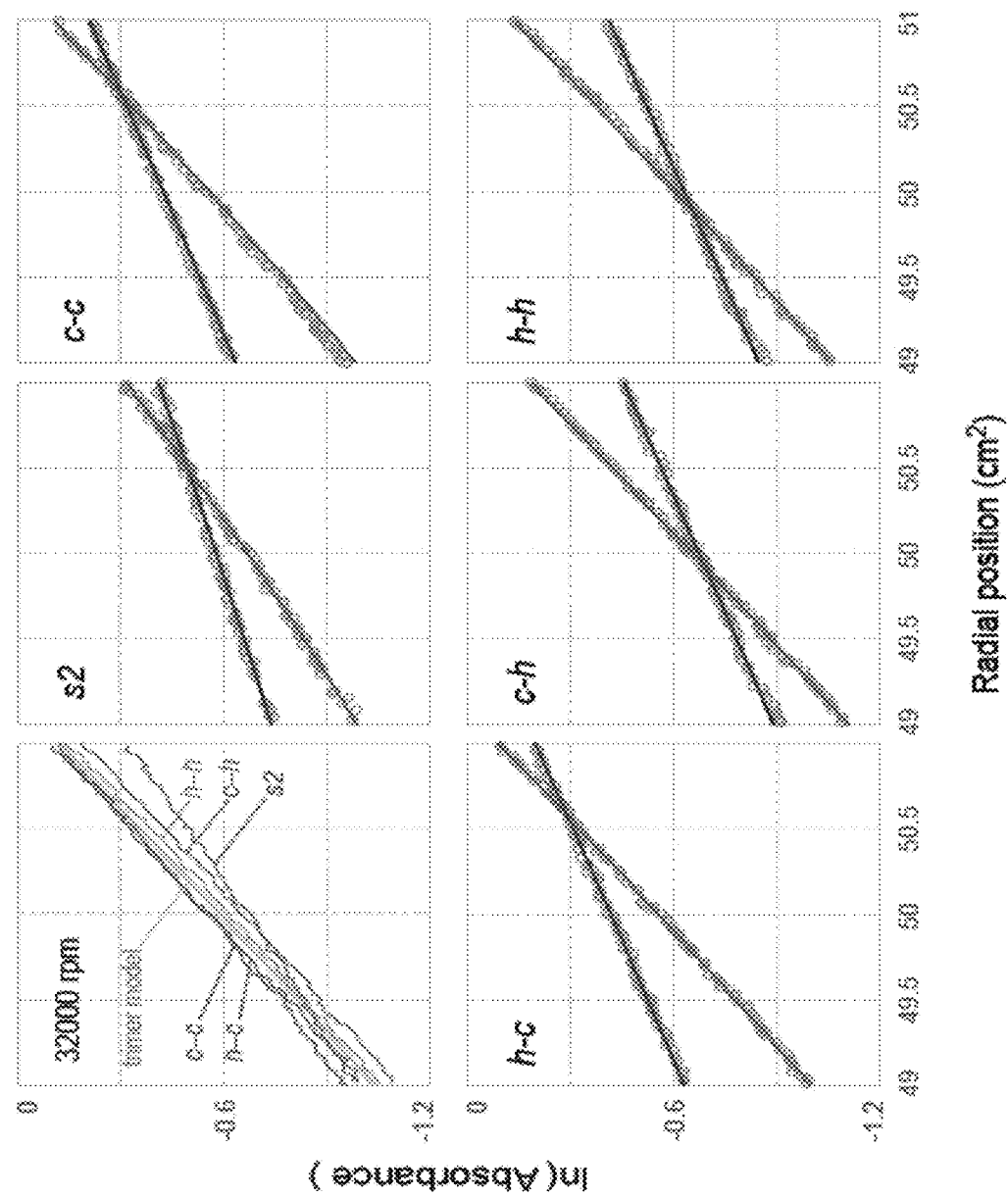
FIG. 5 shows sedimentation equilibrium analysis of x–y·s2 constructs. Equilibrium gradients for linked-dimer—s2 mixtures are shown with models that provide optimal fits. The first panel compares raw data collected at 32 k rpm for all samples with the theoretical model of a trimer, and highlights the difference between gradients for s2 and x–y·s2 constructs. The slope of the computed model represents the gradient expected from a pure, three-stranded unit, whereas its placement on the y-axis is arbitrary. All x–y·s2 constructs form gradients that are similar and match the model predicted for a triple-helical unit. The remaining five panels show gradients formed at 22 and 32 k rpm (gray circles) and models that best fitted the data (solid lines). The s2 data are best described by a mixture of monomers and triple helices, whereas the remaining sets are modeled as single triple-helical species. Although the c-c data suggest the presence of some lower molecular-weight species in solution, constructs featuring the h-c, c-h, and h-h linkers are in good agreement with a triple-helical model.

The disulfide-linked variants share with [(PPG)$_{10}$]$_3$ the characteristic CD signature of a collagen triple helix (FIG. 4A). The variants do, however, exhibit greater mean ellipticity at 226 nm than does (PPG)$_{10}$ (SEQ ID NO:6). Triple-helical association was confirmed in sedimentation equilibrium experiments with AUC. Whereas gradients formed by x–y·s2 constructs are readily described by a triple-helical model, (PPG)$_{10}$ (SEQ ID NO:6) appears as a mixture of monomers and trimers. Thus, the covalent linking of strands appears not only to accommodate and promote triple-helix formation, but also to increase trimer content (FIG. 5).

Figure 6:
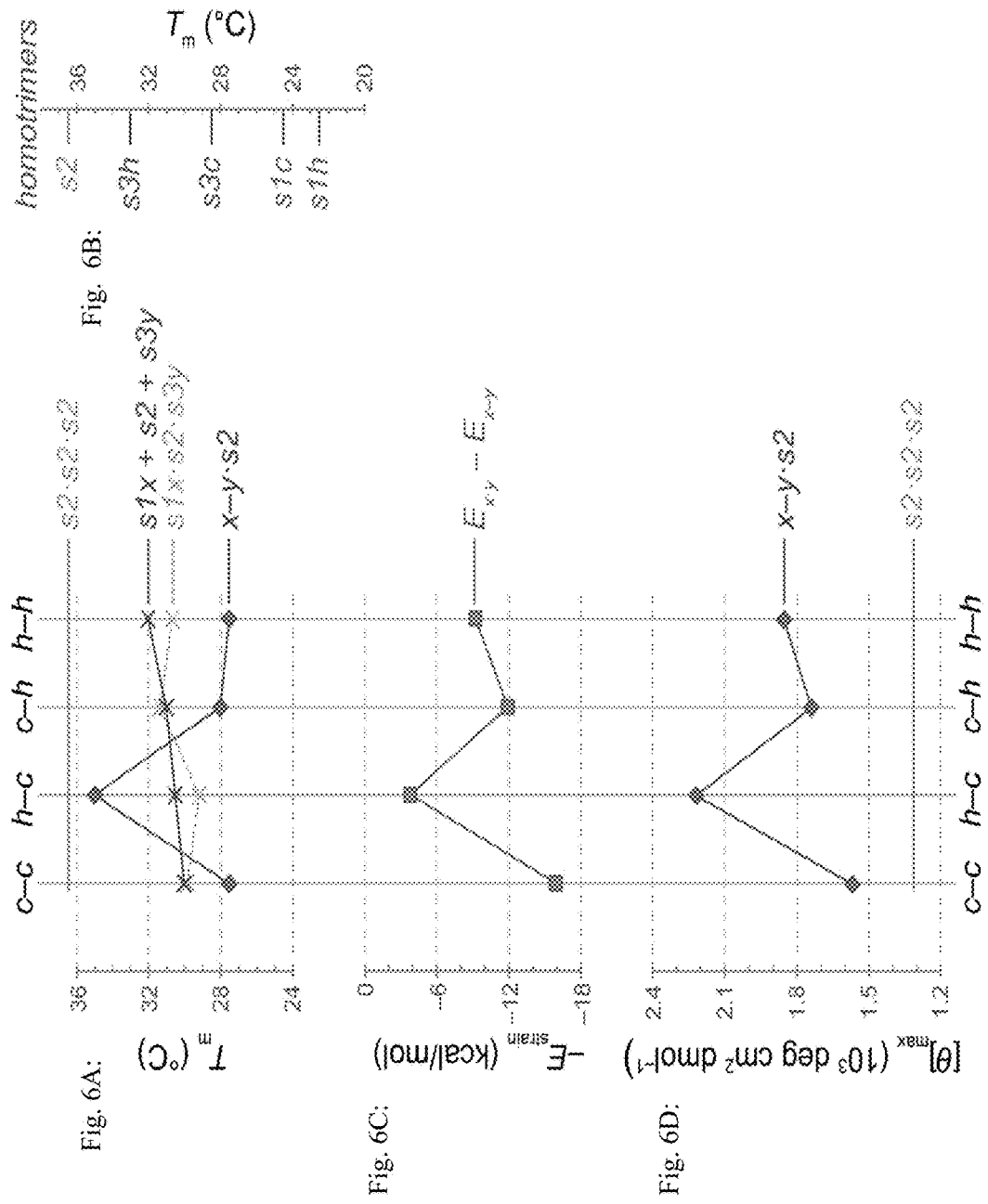
FIGS. 6A, 6B, 6C, and 6D show comparison of experimental and computational data for x–y·s2 and related triple helices.

A marked loss in the thermostability of triple helices was observed for all disulfide-linked variants, except that with an h-c bridge (FIGS. 4B and 6A). Use of a c-c, c-h, or h-h bridge leads to a 9-° C. decrease in the value of $T_m$, from 37 to 28° C. In contrast, trimers that feature an h-c bridge ($T_m$=35° C.) do not experience significant destabilization, as predicted by computational analysis.

The large destabilizing effect of replacing a proline residue with Cys or Hcy (FIG. 6B) obfuscates comparisons of a stapled triple helix (x–y·s2) with an unmodified trimer (s2·s2·s2). A more appropriate comparison would be with a trimer containing reduced Cys or Hcy (s1x·s2·s3y). A linear relationship exists between the free energy of stabilization and $T_m$ value of CMPs (see Persikov, A. V.; Ramshaw, J. A. M.; Brodsky, B. *J. Biol. Chem.* 2005, 280, 19343-19349). If interstrand interactions of reduced Cys and Hcy in a triple helix are insignificant, then the value of $T_m$ for an s1x·s2·s3y heterotrimer can be estimated from the value for homotrimers. Values of $T_m$ thus predicted are 30-32° C. for all s1x·s2·s3y heterotrimers.

To verify this prediction, we assessed equimolar mixtures of s1x, s2, and s3y in thermal denaturation experiments. The resulting $T_m$ values near 31° C. for "reduced" x·y·s2 complexes agree closely with the predicted values (FIG. 6A; solid vs dotted line). Accordingly, we conclude that c-c, c-h, and h-h bridges ($T_m$~28° C.) are strained and thus destabilize the triple helix, whereas only an h-c bridge is stabilizing ($T_m$ 35° C.) (FIG. 6A; solid vs solid line).

Our calculations correctly predict the h-c bridge to be the least strained and thus most stabilizing linker. Still, for strained linkers the $T_m$ values do not correlate with computational rankings (cf. FIGS. 6A and 6C). The computational models for strained linkers feature high-energy regions that cannot relax due to backbone constraints. In reality, backbone distortions lower the overall energy of these structures, though rendering them less collagen-like. Indeed, we observe evidence for this relaxation in the signal intensity at the diagnostic wavelength (~225 nm) in the CD spectrum, as the rank order of the maximum CD signal is in perfect agreement with the rank order of $-E_{strain}$ for x-y·s2 triple helices (cf: FIGS. 6C and 6D).

We propose the Hcy-Cys interstrand disulfide bridge as a superior alternative to Cys-Cys for collagen-like peptides and proteins. We expect facile integration of this staple into Xaa-Yaa-Gly repeats, as Hcy-Cys bridges conform well to the collagen fold. Self-assembling systems that grow through the sticky-ended assembly of triple-helical units rely on two interstrand bridges and will benefit from our discovery (see, e.g., Koide, T.; Homma, D. L.; Asada, S.; Kitagawa, K. *Bioorg. Med. Chem. Let.* 2005, 15, 5230-5233; Yamazaki, C. M.; Asada, S.; Kitagawa, K.; Koide, T. *Biopolymers* 2008, 90, 816-823; Yamazaki, C. M.; Kadoya, Y.; Hozumi, K.; Okano-Kosugi, H.; Asada, S.; Kitagawa, K.; Nomizu, M.; Koide, T. *Biomaterials* 2010, 31, 1925-1934). Hcy-Cys bridges should improve kinetics and stability of such assemblies, and allow for smaller assembling units. We expect Hcy-Cys bridges to extend the reach of self-assembling collagen-like biomaterials.

Computational Methodology and Results.

Computational Design and Evaluation of Disulfide Bridges Between (PPG)$_{10}$ Strands.

All calculations were performed on Intel Xeon 2.33-GHz processors at the Materials and Process Simulation Center in California Institute of Technology (Pasadena, Calif.). Computational models were built on the crystal structure of the (PPG)$_{10}$ trimer (PDB entry 1kf6) (Berisio, R.; Vitagliano, L.; Mazzarella, L.; Zagari, A. *Protein Sci.* 2002, 11, 262-270). Hydrogens were added using Reduce (Word, J. M.; Lovell, S. C.; Richardson, J. S.; Richardson, D. C. *J. Mol. Biol.* 1999, 285, 1735-1747) (ver. 3.03), and the model was fully minimized. All minimizations were carried out to a 0.2 kcal/mol/Å RMS-force convergence criterion using conjugate gradient minimization on MPSim (Lim, K. T.; Brunett, S.; Iotov, M.; McClurg, R. B.; Vaidehi, N.; Dasgupta, S.; Taylor, S.; Goddard, W. A. *J. Comput. Chem.* 1997, 18, 501-521) without solvation. The forces on the model peptides were described by the DREIDING force-field (Mayo, S. L.; Olafson, B. D.; Goddard, W. A. *J. Phys. Chem.* 1990, 94, 8897-8909) without atomic charges. Following initial optimization, the backbone coordinates of the trimeric structure were set to be immutable, and were kept that way throughout.

Proline residues in the Xaa and Yaa positions selected for linkage were replaced with Cys, Hcy, or Tnv. The new side-chains were minimized on trimers that contain both Cys-analogs on neighboring positions, and the pre-disulfide formation energies, $E_{x\cdot y}$ were determined. The thiol hydrogens were omitted from these models to maintain the same number of atoms before and after disulfide formation. The configurations of the disulfide-bonded linkers were optimized, first by minimization and then by multiple rounds of simulated annealing. Post-disulfide formation energies, $E_{x\cdot y}$ were determined on the resulting models. The energy change due to disulfide formation was calculated as $E_{strain}=E_{x\cdot y}-E_{x\cdot y}$. The intent of this metric is to quantify changes in bonding and steric interactions, and allow their comparison across linkers. The omission of solvation and Coulombic contributions from the model help reduce noise and focus results on local interactions.

Linker Strain in Relation to Torsion Angles.

The h-c linker is predicted to be least strained by the computational analysis, as shown in Table S1. Strained bond lengths and bond angles are responsible for the poor performance of c-c and c-h linkers, whereas high torsion energies and, for t-t and t-c, van der Waals energies are observed for linkers other than h-c. Overall, linkers that have a longer side chain at the Xaa position than Yaa ($n_{Xaa}>n_{Yaa}$) perform better than those with shorter ($n_{Xaa}<n_{Yaa}$) or analogous side chains ($n_{Xaa}=n_{Yaa}$). The torsion angles across each C—C, C—S, or S—S bond on the linker models are presented in Table 2. The C—C and C—S torsion angles on the linkers can be categorized into two groups: near-eclipsed ($|\chi|=0°-30°$ or $90°-150°$) or near-staggered ($|\chi|=30°-90°$ or $150°-180°$). The high torsion energies correlate with the occurrence of near-eclipsed torsion angles across C—C bonds, most often between $C^\beta$ and $C^\gamma$. The h-c linker is the only one that does not harbor strained torsion angles according to this simple criterion.

Experimental Methodology and Results.

Peptide Synthesis.

All (PPG)$_{10}$ (SEQ ID NO:6) and (PPG)$_{10}$-variants were synthesized on Wang or polyethylene glycol-based resins using a Prelude (Protein Technologies) peptide synthesizer at room temperature using standard Fmoc chemistry' at the University of Wisconsin-Madison Biotechnology Center. Condensation of Fmoc-ProProGly-OH tripeptide segments was employed with all peptides wherever applicable, except for the C-terminal PPG section where proline residues were added individually on glycine-preloaded resins. Synthesis of Fmoc-ProProGly-OH was described previously (Jenkins, C. L.; Vasbinder, M. M.; Miller, S. J.; Raines, R. T. *Org. Lett.* 2005, 7, 2619-2622), and Fmoc-S-trityl-L-homocysteine was from Chem-Impex (Wood Dale, Ill.). Fmoc removal was achieved in piperidine (20% v/v in DMF), and peptide building blocks (4 equiv), activated through treatment with HCTU and NMM, were coupled to the free amine of the growing chain for 60 min.

Peptides were cleaved from the resin and deprotected in reagent R (90:5:3:2 TFA:thioanisole:ethanedithiol:anisole; 1.5-2.0 mL), precipitated from methyl t-butyl ether below 0° C., and isolated by centrifugation. Dried crude peptides were dissolved in 0.1% v/v TFA and filtered and purified by preparative HPLC at 45° C. using gradients of CH$_3$CN/water containing 0.1% v/v TFA on a Shimadzu Prominence unit equipped with a Macherey-Nagel VarioPrep 250/21 C18 column. All peptides were >90% pure according to analytical HPLC and MALDI-TOF mass spectrometry (MS). MALDI-TOF analysis was carried out on an Applied Biosystems Voyager DE-Pro mass spectrometer at University of Wisconsin-Madison Biophysics Instrumentation Facility (BIF). Both single peptides and linked-dimers were analyzed using a 10:1 matrix mixture of 2-(4-hydroxyphenylazo)benzoic acid: α-cyano-4-hydroxycinnamic acid to suppress the reduction of disulfide bonds due to in-source decay (see Huwiler, K. G.; Mosher, D. F.; Vestling, M. M. *J. Biomol. Tech.* 2003, 14, 289-297).

Synthesis of Linked-Dimers.

Disulfide-linked strand dimers were produced by coupling 2,2'-dithiobis(5-nitropyridine)-(DTNP)-activated thiols on an s3y strand with free thiols on an s1x strand (FIG. 3), as described previously (Rabanal, F.; DeGrado, W. F.; Dutton, P. L. *Tetrahedron Lett.* 1996, 37, 1347-1350; Ottl, J.; Moroder, L. *J Am. Chem. Soc.* 1999, 121, 653-661). Briefly, dried s3y peptides (1.2-1.4 mM) and DTNP (5 equiv) were dissolved in reaction solvent (3:1 v/v HOAc:water; degassed and argon-saturated), and the resulting solution was stirred vigorously for ≥6 h. The reaction was stopped by addition of 1.5 reaction-volumes of HOAc. The reaction mixture was freeze-dried, sonicated in aqueous 0.1% v/v TFA, and filtered through a 0.2-μm membrane. DTNP and 5-nitro-2-pyridinethiol remaining in the freeze-dried filtrate were removed by washing (3×) the lyophilized powder with diethyl ether:methylene chloride (7:3, v/v). Isolated s3y-Npys was freeze dried and weighed.

Figure 7:
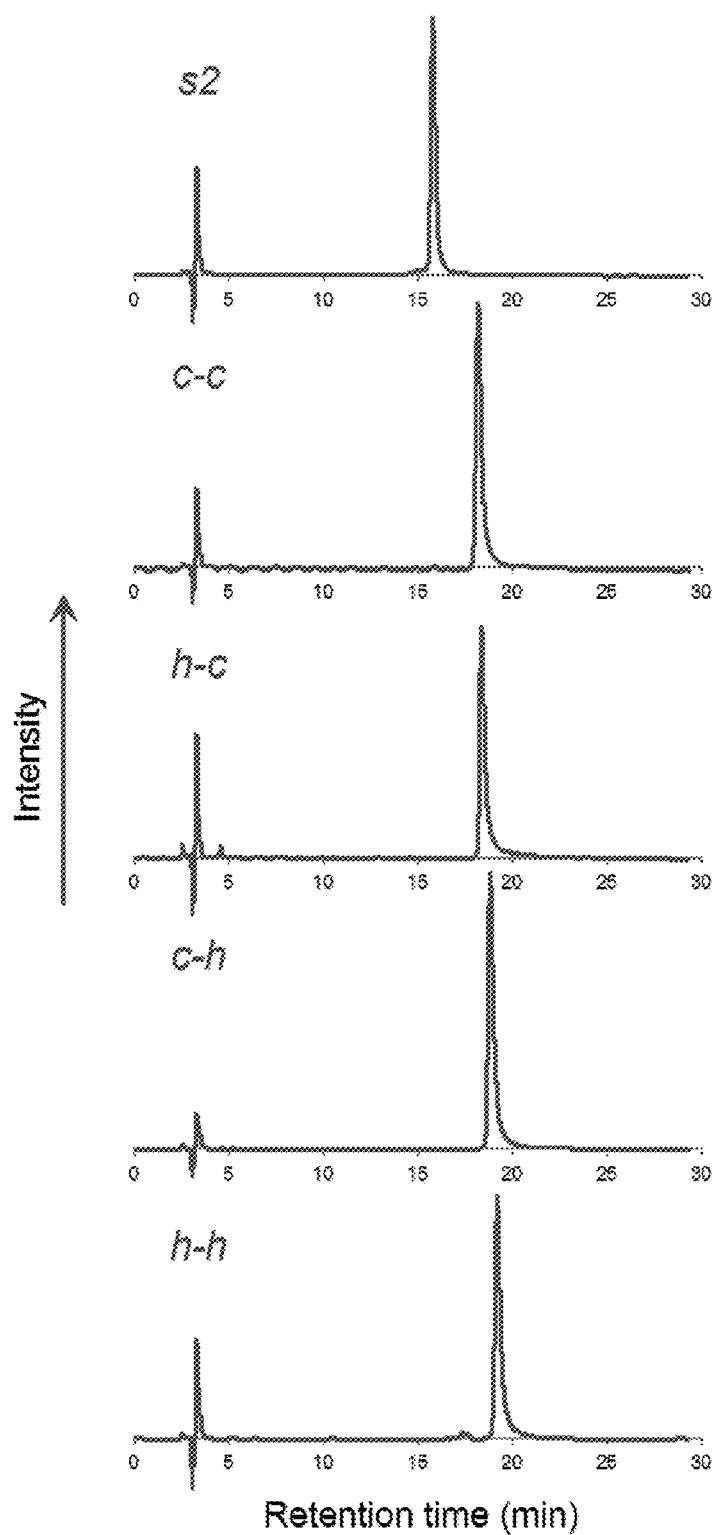
FIG. 7 shows analytical HPLC chromatograms for linked-dimers and the s2 peptide in 50 mM HOAc, as acquired after purification.

Coupling of s1x and s3y-Npys was initiated by mixing equimolar amounts of the components (2.2 mM final concentration) dissolved previously in degassed and argon-saturated 50 mM $NH_4OAc$ buffer, pH 5.3. Reactions were stirred under argon for ≥6 h, after which the solution was acidified and the solvent was removed by lyophilization. Disulfide-linked s1x-s3y dimers were isolated by HPLC and analyzed by MALDI-TOF mass spectrometry as described above. For x-y linked-dimers, (m/z) $[M+H]^+$ calcd 5072.8, found 5073.2 for c-c; calcd 5086.8, found 5086.1 for c-h; calcd 5100.8, found 5100.6 for h-h; calcd 5086.8, found 5086.3 for h-c; calcd 2530.3, found 2530.0 for s2. Analytical HPLC results for purified linked-dimers in 50 mM HOAc are presented in FIG. 7.

Sample Preparation.

Samples were prepared and experiments were conducted as reported previously (Kotch, F. W.; Raines, R. T. *Proc. Natl. Acad. Sci. U.S.A.* 2006, 103, 3028-3033). All peptides and linked dimers were dissolved in 50 mM AcOH to 0.7 mM concentration based on weight. Many of the critical experiments in this study involve mixtures of peptides and linked dimers, and preparation of equimolar mixtures of the components is of vital importance. To ensure equimolar mixtures, relative concentrations were determined by monitoring peptides at 214 nm on the HPLC, and concentrations of all components in interrogated samples were matched to that of 60 μM s2 peptide. The extinction coefficients of all strands were assumed to be identical at 214 nm. The common presence of s2 in all mixtures allows for consistent concentrations across all samples prepared. To facilitate the formation of the thermodynamic product for peptide association, mixtures were heated to ≥55° C., and annealed to 4° C. over 4 h. Samples were left at 4° C. for at least 48 h before data acquisition.

Circular Dichroism (CD) Spectroscopy.

CD spectra for all samples were acquired at 4° C. with a 1-nm band-pass in quartz cuvettes with a 0.1-cm pathlength, using an averaging time of 3 s. For thermal denaturation experiments the CD signal was monitored at 226 nm while the sample was heated from 4 to 64° C. in 3-° C. steps over 4.5 h. All samples were prepared at a strand concentration of 180 μM except for s1x+s2+s3y mixtures, which were prepared at a total peptide concentration of 270 μM in anticipation of complex melting transitions. Due to weak signal, the s1h peptide was tested at 360 μM as well as 180 μM to allow for a more accurate determination of the $T_m$ value. CD data from denaturation experiments were converted to fraction folded, and data near 50% folded were used to obtain the $T_m$ values for each sample, which are reported in Table 3.

TABLE 3

Values of $T_m$ (° C.) for Hetero- and Homotrimers as Determined by Thermal Denaturation Experiments Monitored by Circular Dichroism Spectroscopy

| Linker type | x − y · s2 | Strands that constitute x − y · s2 s1x, s2, s3y | s1x · s2 · s3y (calculated)[a] | s1x + s2 + s3y mixture |
|---|---|---|---|---|
| c-c | 28 | 25, 37, 29 | 30 | 30 |
| h-c | 35 | 22, 37, 29 | 29 | 30 |
| c-h | 28 | 25, 37, 33 | 31 | 31 |
| h-h | 27 | 22, 37, 33 | 31 | 32 |

[a]The estimate of the $T_m$ for "reduced" x − y · s2 was calculated as the average of the homotrimer $T_m$ values for the related s1x, s2 and s3y strands.

Figure 8:
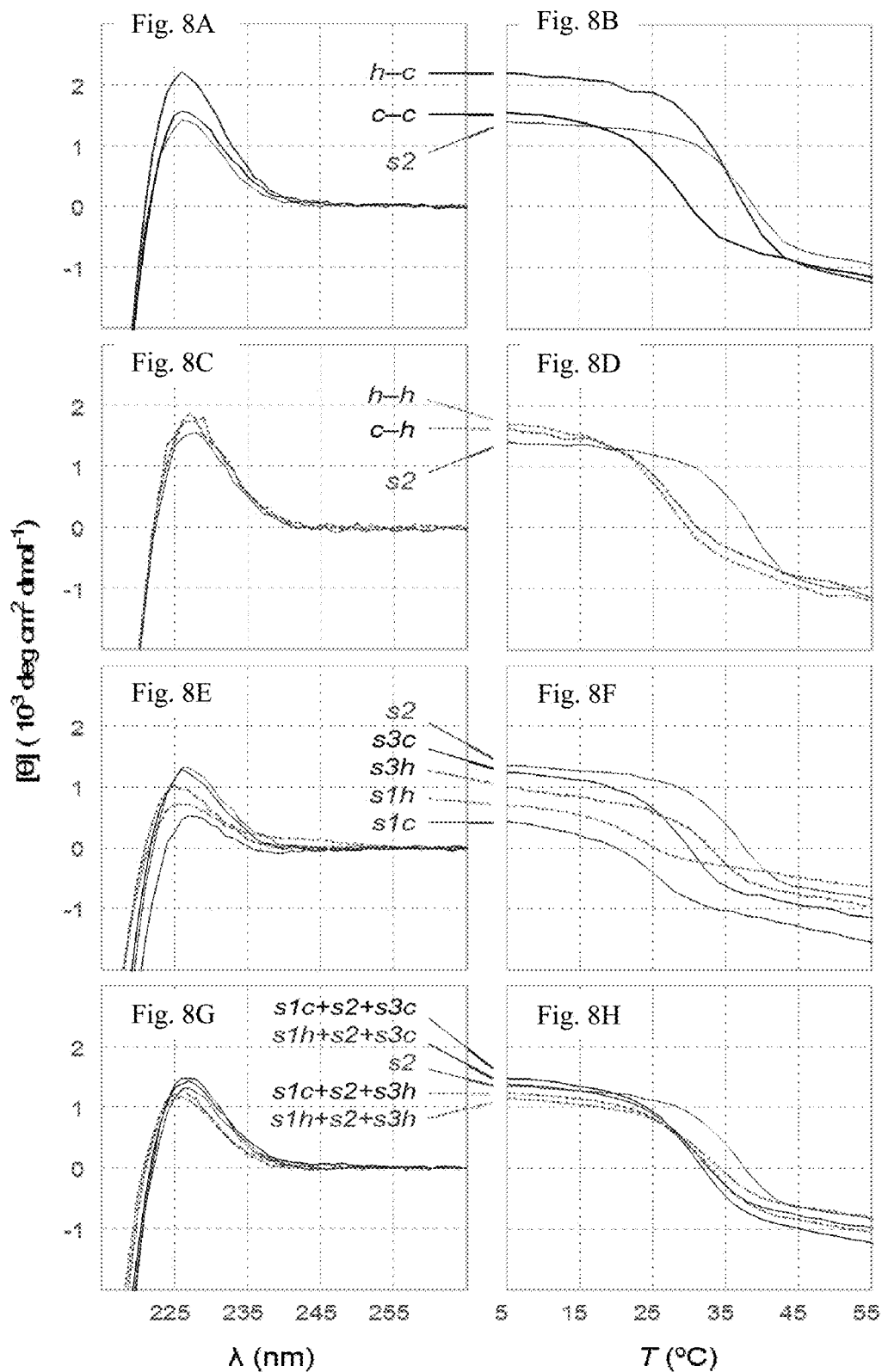
FIG. 8.

CD data were acquired on CD spectrometers from Aviv Biomedical (Lakewood, N.J.). These spectrometers were an Aviv 202SF and 420 in the BIF, and an Aviv 420 in the Gellman Laboratory of the Department of Chemistry, all of them equipped with a 5-cell thermoelectric sample changer. Data on 180 μM s2 were collected in every experiment to allow comparison of instrument performance and to account for differences in wavelength calibration. Our results were well reproducible between instruments ($T_m$=36.5±0.6° C. for 180 μM s2; n=5). All CD spectra and melting curves are discussed in this study are shown in FIG. 8.

Analytical Ultracentrifugation (AUC).

Sedimentation equilibrium experiments were performed at the BIF with a Beckman XL-A analytical ultracentrifuge equipped with an An-60 Ti rotor. Samples were prepared at a strand concentration of 180 μM, but were diluted to a concentration of 90 μM before the experiment. Sample (100 μL) and buffer (110 μL) were placed in a cell with a 12-mm double-sector charcoal-filled centerpiece (Epon). Experiments were run at 4° C. at speeds of 12, 22, 32, and 42 k rpm, and gradients recorded at 231 nm were monitored until they were superimposable when recorded 4 h apart. A buffer density of 1.00037 g/mL and a partial specific volume of 0.7275 mL/g calculated based on amino acid content for $(PPG)_{10}$ was used. Equilibrium gradients at 4° C. were modeled as single and multiple non-interacting species through nonlinear least-squares fits to gradient data. Analysis was performed with programs written for IGOR PRO (WaveMetrics, Lake Oswego, Oreg.) by D. R. McCaslin (University of Wisconsin). Non-sedimenting baselines between 0.03-0.05 OD were applied for all samples, whereas 0.07 OD was used for the x−y·s2 construct featuring a c-c linker. Plots of gradients and fits are shown in FIG. 5.

Overall, the data collected on x−y·s2 variants fitted best to a triple-helical model (single species with MW=7.6 kDa). A similar model does not explain the s2 data. In addition to triple helices, consideration of free $(PPG)_{10}$ strands in the model was necessary for satisfactory description of s2 gradients. Among x−y·s2 variants, the samples that feature h-c, c-h and h-h linkers behave as triple-helical units. Even though the c-c case forms gradients similar to others, models that consider triple-helices work best either with large baseline corrections, or when strand-dimers are considered in the model in addition to triple helices. It is likely that the actual composition for this sample includes triple helices, together with low levels of strand-monomers and dimers. Such issues are not observed with linkers predicted to be less strained.

Example 2: Comparisons Among Interstrand Disulfide and Thioether Bridges

Figure 9:
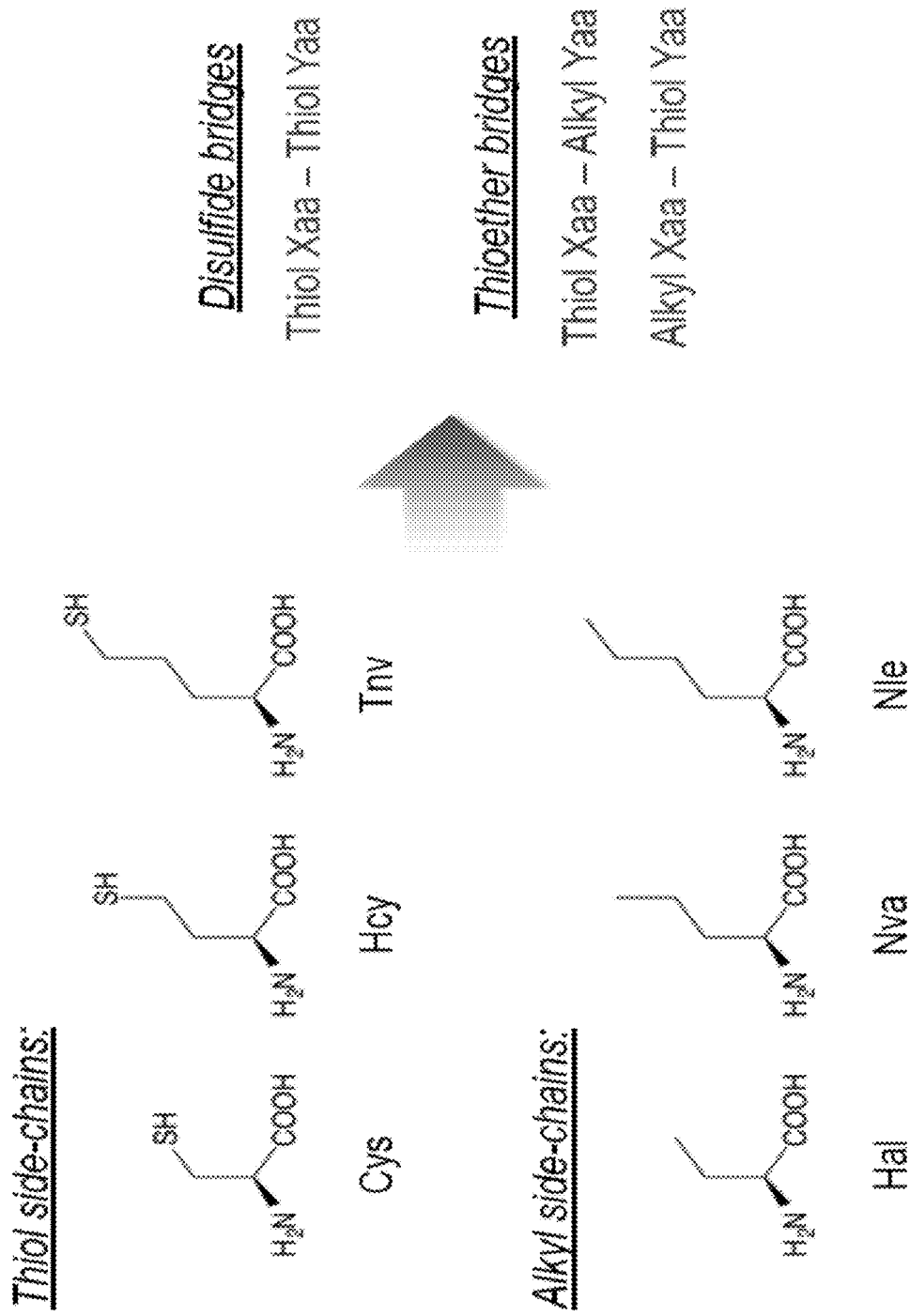
FIG. 9 shows the amino acid residues considered and the disulfide bridge and thioether bridge residue combinations compared in Example 2.

In this example, we extended the evaluation of the disulfide bridges reported in Example 1 to analogous thioether bridges having the sulfur atom in the thiol side chain of a cysteine (Cys), homocysteine (Hcy), or thionorvaline (Tnv) residue in one CMP strand covalently bonded to the terminal carbon atom in the alkyl side chain of a homoalanine (Hal), norvaline (Nva), or norleucine (Nle) residue in an adjacent CMP strand. Such bonds can be built and assessed in silico. However, as the skilled artisan would understand, thioether linkages are chemically synthesized by directly forming such covalent bonds. The disulfide bridges having the sulfur atom in the thiol side chain of a cysteine (Cys), homocysteine (Hcy), or thionorvaline (Tnv) residue in one CMP strand covalently bonded to the sulfur atom in the thiol side chain of a cysteine (Cys), homocysteine (Hcy), or thionorvaline (Tnv) residue in an adjacent CMP strand, as previously described in Example 1, were also included in this comparison. The structures of the listed amino acid residues and a schematic of the evaluated combinations is shown in FIG. 9.

Accordingly, this Example summarizes the data for 23 different covalent bridges between an Xaa residue of a first CMP strand and a Yaa residue of a second CMP strand. These 23 bridges include the nine disulfide bridge combinations disclosed in Example 1 (Xaa-Yaa is Cys-Cys, Cys-Hcy, Cys-Tnv, Hcy-Cys, Hcy-Hcy, Hcy-Tnv, Tnv-Cys, Tnv-Hcy, or Tnv-Tnv), and 14 additionally disclosed thioether bridge combinations (Xaa-Yaa is Cys-Hal, Cys-Nva, Cys-Nle, Hcy-Hal (or the equivalent, Hal-Hcy), Hcy-Nva (or the equivalent, Hal-Tnv), Hcy-Nle, Tnv-Hal (or the equivalent, Nva-Hcy), Tnv-Nva (or the equivalent, Nva-Tnv), Tnv-Nle, Hal-Cys, Nva-Cys, Nle-Cys, Nle-Hcy, or Nle-Tnv).

$E_{strain}$ for each of each of these 23 Xaa-Yaa bridges was calculated using the methods described in Example 1. Table 4 presents the results grouped by bridge length (i.e., from 3 to 7 bonds between linker (3-carbon atoms), then ordered within each group from low to high total $E_{strain}$. Table 5 presents the same results ordered from low to high total $E_{strain}$, without regard to bridge length. The sum of bond and angle strain components to $E_{strain}$ are reported together under "Bonds" in both tables.

Figure 10A:
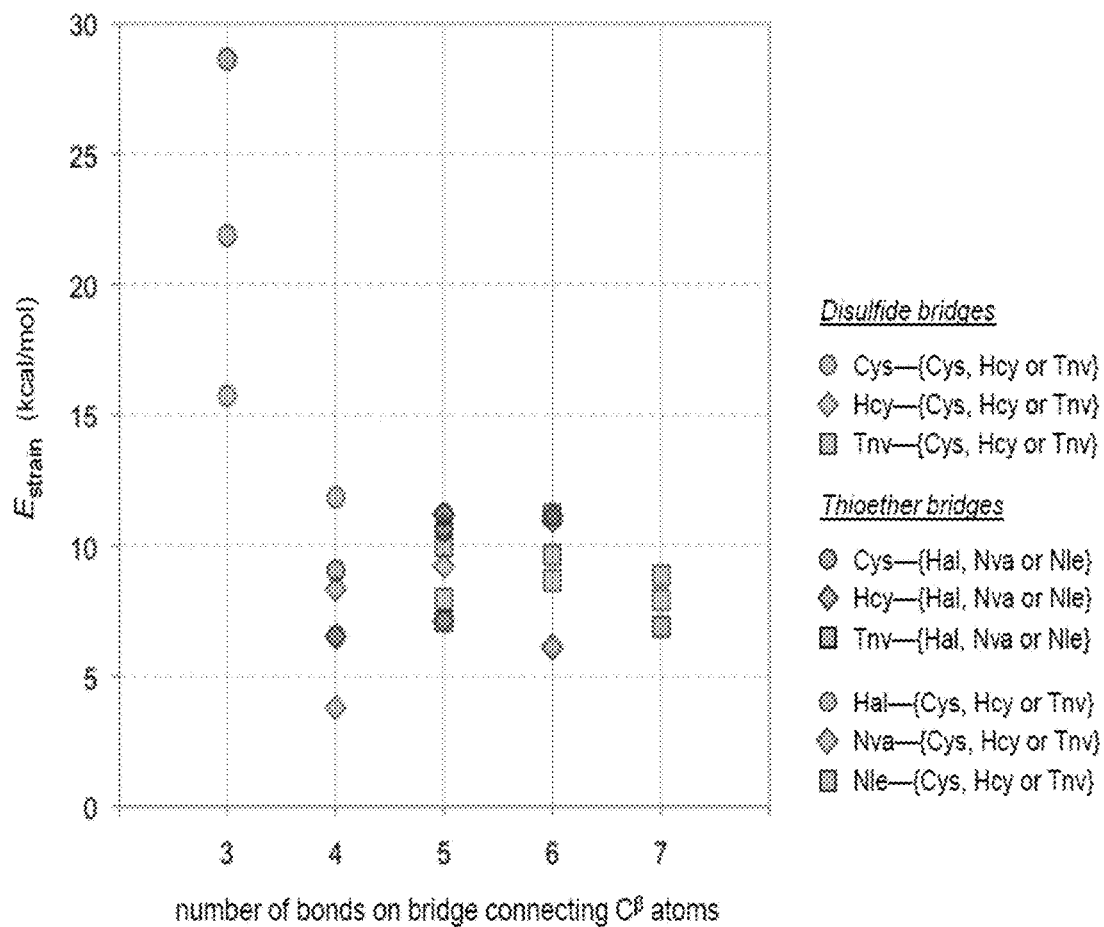
FIG. 10A is a graph showing $E_{strain}$ as a function of the number of bonds connecting the Xaa and Yaa $C^\beta$ atoms on the interstrand bridge. The $E_{strain}$ for each interstrand bridge is plotted separately. The results show the substantially reduced $E_{strain}$ for the Hcy-Cys Xaa-Yaa interstrand disulfide bridge, as compared to other tested combinations.
Figure 10B:
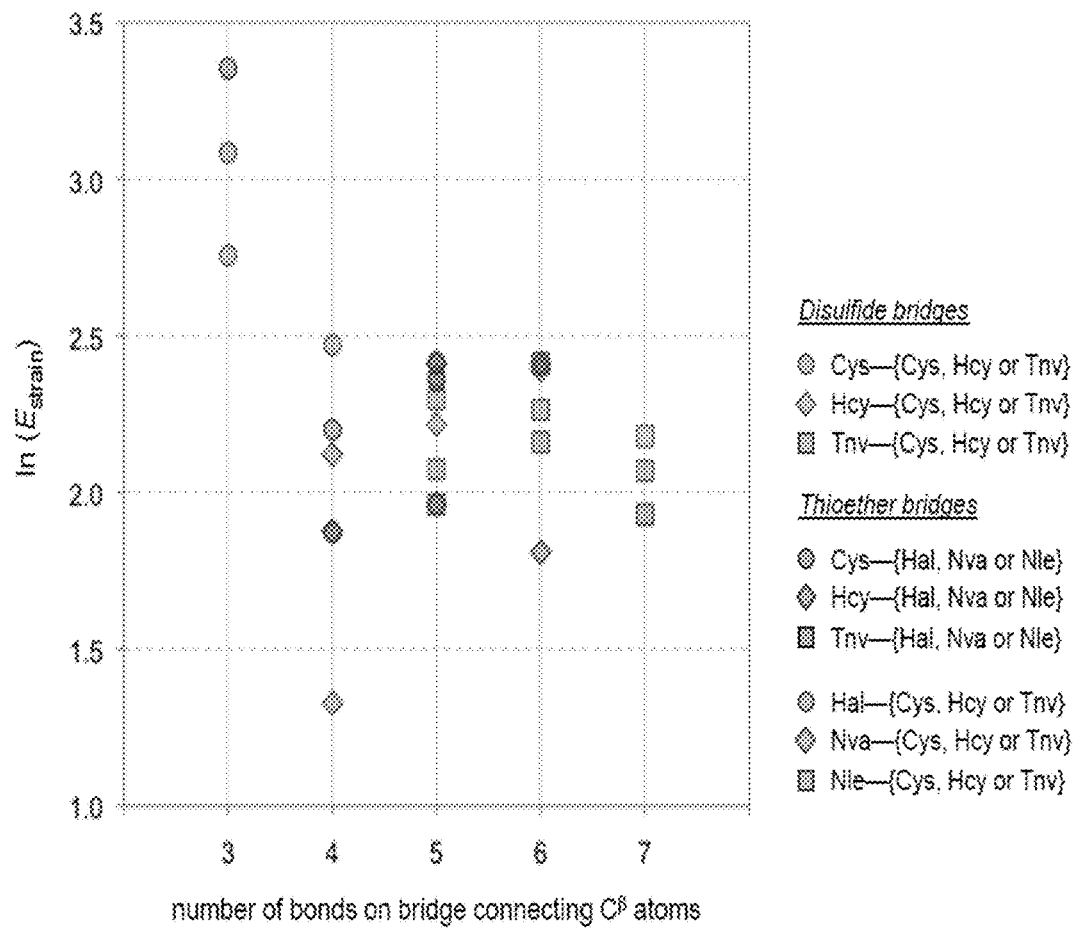
FIG. 10B is a graph showing natural log of $E_{strain}$ as a function of the number of C—C bonds in the interstrand bridge. The $E_{strain}$ for each interstrand bridge is plotted separately. The results show the substantially reduced $E_{strain}$ for the Hcy-Cys Xaa-Yaa interstrand disulfide bridge, as compared to other tested combinations.
Figure 11:
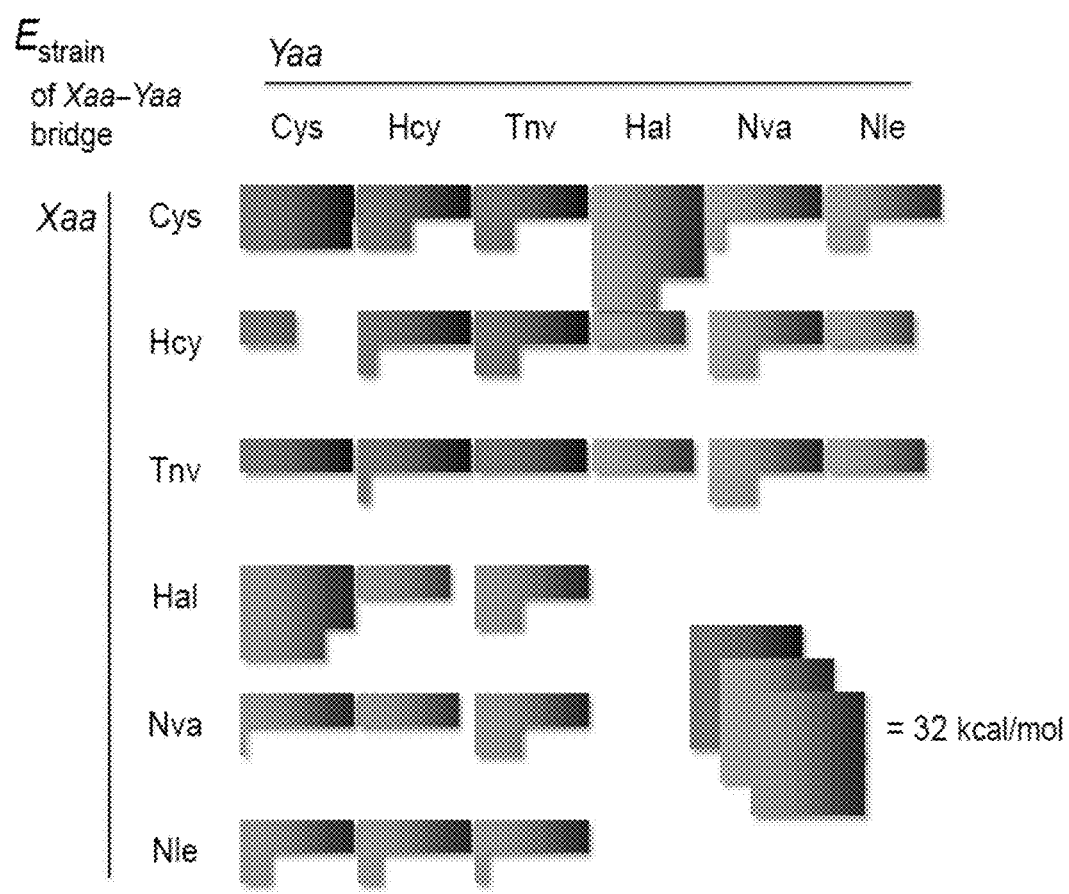
FIG. 11 is a graph visually showing $E_{strain}$ of each of the 27 tested combinations represented by the 2-dimensional surface area of shape shown for each combination. For comparison, the surface area of the squares shown on the bottom right represent an $E_{strain}$ of 32 kcal/mole. The graph illustrates the substantially reduced $E_{strain}$ for the Hcy-Cys Xaa-Yaa interstrand disulfide bridge, as compared to other tested combinations.

As in Example 1, the disulfide Xaa-Yaa bridge comprising Hcy-Cys had substantially lower $E_{strain}$ than any other bridge. The results are shown graphically in FIGS. 10A, 10B, and 11. The substantially improved $E_{strain}$ of the Hcy-Cys Xaa-Yaa disulfide bridge as compared to the other 22 tested combinations is particularly dramatic when presented logarithmically (FIG. 10B) or as a visual surface area comparison (FIG. 11). Replacement of either of the sulfur atoms on the Hcy-Cys disulfide bridge with a methylene group nearly doubles the $E_{strain}$ value of the Hcy-Hal and Nva-Cys thioether bridges thereby created. The substantial superiority of the Hcy-Cys Xaa-Yaa disulfide bridge was both unexpected and surprising, and will be applied to make improved CMP systems and structures for biomedical and other applications.

TABLE 4

$E_{strain}$ and its components for disulfide- and thioether-linkages (ranked by linker size, then $E_{strain}$)

| | $E_{strain}$ components (kcal/mol) | | | | # of bonds | | Linker |
|---|---|---|---|---|---|---|---|
| Xaa x Yaa | Total | Bonds | Torsion | VDW | btw. $C^\beta$ atoms | | $C^\beta$-to-$C^\beta$ |
| Cys x Cys | 15.8 | 10.3 | 4.5 | 1.2 | 3 | | CSSC |
| Hal x Cys | 21.9 | 15.2 | 3.6 | 3.1 | 3 | | CCSC |
| Cys x Hal | 28.6 | 19.3 | 5.7 | 3.7 | 3 | | CSCC |
| Hcy x Cys | 3.8 | 0.9 | 2.3 | 0.6 | 4 | | CCSSC |
| Hcy x Hal | 6.5 | 1.1 | 3.6 | 1.9 | 4 | eq. Hal x Hcy | CCSCC |
| Hal x Hcy | 6.5 | 1.1 | 3.6 | 1.9 | 4 | eq. Hcy x Hal | CCSCC |
| Nva x Cys | 8.3 | 2.4 | 3.6 | 2.4 | 4 | | CCCSC |
| Cys x Nva | 9.0 | 1.8 | 4.7 | 2.7 | 4 | | CSCCC |
| Cys x Hcy | 11.8 | 4.7 | 5.3 | 1.9 | 4 | | CSSCC |
| Tnv x Hal | 7.1 | 2.4 | 2.3 | 2.4 | 5 | eq. Nva x Hcy | CCCSCC |
| Nva x Hcy | 7.1 | 2.4 | 2.3 | 2.4 | 5 | eq. Tnv x Hal | CCCSCC |
| Tnv x Cys | 8.0 | 1.6 | 2.5 | 3.9 | 5 | | CCCSSC |
| Hcy x Hcy | 9.2 | 1.3 | 5.8 | 2.0 | 5 | | CCSSCC |
| Nle x Cys | 10.0 | 3.9 | 4.4 | 1.7 | 5 | | CCCCSC |
| Cys x Nle | 10.6 | 1.7 | 5.6 | 3.3 | 5 | | CSCCCC |
| Cys x Tnv | 10.7 | 1.8 | 6.7 | 2.3 | 5 | | CSSCCC |
| Hcy x Nva | 11.2 | 1.2 | 6.1 | 3.9 | 5 | eq. Hal x Tnv | CCSCCC |
| Hal x Tnv | 11.2 | 1.2 | 6.1 | 3.9 | 5 | eq. Hcy x Nva | CCSCCC |
| Hcy x Nle | 6.1 | 0.9 | 3.6 | 1.6 | 6 | | CCSCCCC |
| Tnv x Hcy | 8.7 | 1.4 | 5.6 | 1.7 | 6 | | CCCSSCC |
| Nle x Hcy | 9.6 | 2.5 | 3.8 | 3.4 | 6 | | CCCCSCC |
| Hcy x Tnv | 11.0 | 2.4 | 5.0 | 3.6 | 6 | | CCSSCCC |
| Tnv x Nva | 11.2 | 3.2 | 5.6 | 2.4 | 6 | eq. Nva x Tnv | CCCSCCC |
| Nva x Tnv | 11.2 | 3.2 | 5.6 | 2.4 | 6 | eq. Tnv x Nva | CCCSCCC |
| Tnv x Nle | 6.9 | 0.3 | 3.8 | 2.9 | 7 | | CCCSCCCC |
| Tnv x Tnv | 7.9 | 1.8 | 2.6 | 3.5 | 7 | | CCCSSCCC |
| Nle x Tnv | 8.8 | 1.3 | 4.1 | 3.4 | 7 | | CCCCSCCC |

TABLE 5

$E_{strain}$ and its components for disulfide- and thioether-linkages (ranked by $E_{strain}$)

| Xaa x Yaa | $E_{strain}$ components (kcal/mol) | | | | # of bonds btw. $C^\beta$ atoms | Linker $C^\beta$-to-$C^\beta$ |
|---|---|---|---|---|---|---|
| | Total | Bonds | Torsion | VDW | | |
| Hcy x Cys | 3.8 | 0.9 | 2.3 | 0.6 | 4 | CCSSC |
| Hcy x Nle | 6.1 | 0.9 | 3.6 | 1.6 | 6 | CCSCCCC |
| Hcy x Hal | 6.5 | 1.1 | 3.6 | 1.9 | 4 eq. Hal x Hcy | CCSCC |
| Hal x Hcy | 6.5 | 1.1 | 3.6 | 1.9 | 4 eq. Hcy x Hal | CCSCC |
| Tnv x Nle | 6.9 | 0.3 | 3.8 | 2.9 | 7 | CCCSCCCC |
| Tnv x Hal | 7.1 | 2.4 | 2.3 | 2.4 | 5 eq. Nva x Hcy | CCCSCC |
| Nva x Hcy | 7.1 | 2.4 | 2.3 | 2.4 | 5 eq. Tnv x Hal | CCCSCC |
| Tnv x Tnv | 7.9 | 1.8 | 2.6 | 3.5 | 7 | CCCSSCCC |
| Tnv x Cys | 8.0 | 1.6 | 2.5 | 3.9 | 5 | CCCSSC |
| Nva x Cys | 8.3 | 2.4 | 3.6 | 2.4 | 4 | CCCSC |
| Tnv x Hcy | 8.7 | 1.4 | 5.6 | 1.7 | 6 | CCCSSCC |
| Nle x Tnv | 8.8 | 1.3 | 4.1 | 3.4 | 7 | CCCCSCCC |
| Cys x Nva | 9.0 | 1.8 | 4.7 | 2.7 | 4 | CSCCC |
| Hcy x Hcy | 9.2 | 1.3 | 5.8 | 2.0 | 5 | CCSSCC |
| Nle x Hcy | 9.6 | 2.5 | 3.8 | 3.4 | 6 | CCCCSCC |
| Nle x Cys | 10.0 | 3.9 | 4.4 | 1.7 | 5 | CCCCSC |
| Cys x Nle | 10.6 | 1.7 | 5.6 | 3.3 | 5 | CSCCCC |
| Cys x Tnv | 10.7 | 1.8 | 6.7 | 2.3 | 5 | CSSCCC |
| Hcy x Tnv | 11.0 | 2.4 | 5.0 | 3.6 | 6 | CCSSSCCC |
| Tnv x Nva | 11.2 | 3.2 | 5.6 | 2.4 | 6 eq. Nva x Tnv | CCCSCCC |
| Nva x Tnv | 11.2 | 3.2 | 5.6 | 2.4 | 6 eq. Tnv x Nva | CCCSCCC |
| Hcy x Nva | 11.2 | 1.2 | 6.1 | 3.9 | 5 eq. Hal x Tnv | CCSCCC |
| Hal x Tnv | 11.2 | 1.2 | 6.1 | 3.9 | 5 eq. Hcy x Nva | CCSCCC |
| Cys x Hcy | 11.8 | 4.7 | 5.3 | 1.9 | 4 | CSSCC |
| Cys x Cys | 15.8 | 10.3 | 4.5 | 1.2 | 3 | CSSC |
| Hal x Cys | 21.9 | 15.2 | 3.6 | 3.1 | 3 | CCSC |
| Cys x Hal | 28.6 | 19.3 | 5.7 | 3.7 | 3 | CSCC |

Example 3: Synthetic Collagen-Like Fibers Through Self-Assembly of Chemically-Linked Triple Helices In previous work, Koide et al. (Bioorg. Med. Chem. Lett. (2005) 15:5230-5233) used two interstrand Cys-Cys disulfide bridges to connect three CMP strands (see FIG. 12A), and showed that such three-stranded units can be used for making larger collagen-like fibrillar assemblies. In our own work (Kotch, F. W.; Raines, R. T. Proc. Natl. Acad. Sci. USA 2006, 103, 3028-3033), we also have synthesized three-stranded CMP units featuring different Cys-Cys interstrand disulfide connectivities, and demonstrated their self-assembly into larger fibrillar structures. Self-assembly of these units into the larger structures progresses through association of their "sticky ends," one- and two-stranded sections of the CMP units, with sticky ends of other such units to produce triple-helices. The methods used in both pioneering studies feature the use of three-stranded constructs that are interconnected with two Cys-Cys disulfide bonds.

Figure 12A:
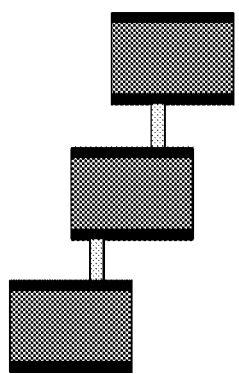
FIG. 12A is a schematic diagram of a three-stranded CMP unit containing two interstrand bridges that could be used for making larger collagen-like fibrillar assemblies, as initially suggested by Koide et al. (*Bioorg. Med. Chem. Lett.* (2005) 15:5230-5233). As disclosed herein, one or both of the interstrand bridges may be an optimized Hcy-Cys interstrand bridge.

In this example, we outline the application of the optimal interstrand disulfide bridge described above to the construction of a three-stranded polypeptide having two separate disulfide bridges between the strands, similar to the generic structure shown in FIG. 12A. Replacement of one or both of the Cys-Cys disulfide bonds with Hcy-Cys linkages should improve the structure and stability of these constructs and enhance material properties of collagen-like fibrillar assemblies they form. Thus, in this example, at least one of these disulfide bridges is a covalent disulfide bond between an Xaa Hcy residue on one CMP strand and a Yaa Cys residue on another CMP strand. The other bridge may be of this type, or may be a conventional Cys-Cys disulfide bridge.

Figure 12B:
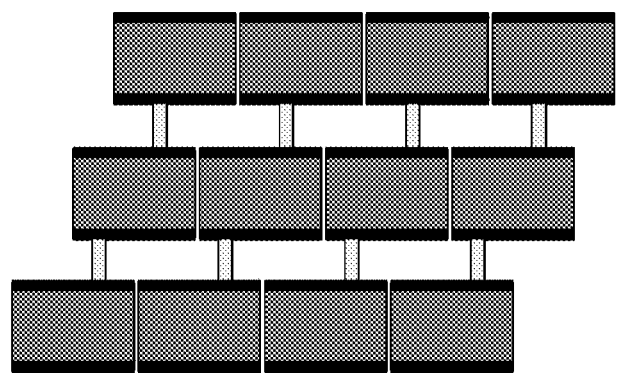
FIG. 12B is a schematic diagram of a larger collagen-like fibrillar assembly that can be self-assembled from multiple CMP units having one or more optimized Hcy-Cys interstrand bridge.

The disclosed Hcy-Cys bridge may be used to produce three chemically-linked strands that could subsequently be used for self-assembly, as described further in Example 4 (see, e.g., FIG. 12B). In one non-limiting example, a three-stranded polypeptide would have the following structure (Hcy-Cys bridge bold and underlined):

(Xaa-Yaa-Gly)$_n$-<u>Hcy</u>-Yaa-Gly-(Xaa-Yaa-Gly)$_m$ (Xaa-Yaa-Gly)$_p$-Xaa-<u>Cys</u>-Gly-(Xaa-Yaa-Gly)$_q$-<u>Hcy</u>-Yaa-Gly-(Xaa-Yaa-Gly)$_r$ (Xaa-Yaa-Gly)$_j$-Xaa-<u>Cys</u>-Gly-(Xaa-Yaa-Gly)$_k$ where (n+m+1)=(p+q+r+2)=(j+k+1). The top line is SEQ ID NO:17, the middle line is SEQ ID NO:21, and the bottom line is SEQ ID NO:23. The two Hcy-Cys disulfide linkages are highlighted.

In some such embodiments, one of the Hcy-Cys linkages may be replaced with Cys-Cys, and utilize the Hcy-Cys bridge in that way. In one non-limiting example, a three-stranded polypeptide would have the following structure (Cys-Cys and Hcy-Cys bridges bold and underlined):

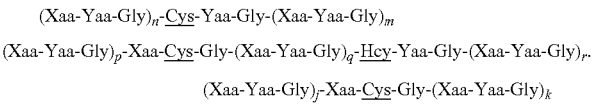

The top line is SEQ ID NO:24, the middle line is SEQ ID NO:21, the bottom line is SEQ ID NO:23. This structure varies from the previous example in that the Hcy-Cys disulfide bridge between the top and middle strands has been replaced with a Cys-Cys disulfide bridge.

In other embodiments, the middle strand may have a sequence that puts the Cys and Hcy in reverse order: (Xaa-Yaa-Gly)$_p$-Hcy-Yaa-Gly-(Xaa-Yaa-Gly)$_q$-Xaa-Cys-Gly-(Xaa-Yaa-Gly)$_r$ (SEQ ID NO:22). In one non-limiting example, a three-stranded polypeptide would have the following structure (Hcy-Cys bridge bold and underlined between strands):

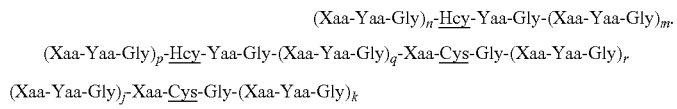

The top line is SEQ ID NO:17, the middle line is SEQ ID NO:23, and the bottom line is SEQ ID NO:23. Assembly would proceed, through sticky ends, as described above.

Example 4: Synthetic Collagen-like Fibers Through the Self-Assembly of Chemically-Linked Strand Pairs In this example, we outline the application of the two-stranded CMP units made with the optimal interstrand disulfide bridge described above (a covalent disulfide bond between an Xaa Hcy residue on one CMP strand and a Yaa Cys residue on another CMP strand) to the construction of larger collagen-like fibrillar assemblies made of a plurality of polypeptides containing the optimal interstrand disulfide bridge.

As noted above, it has been previously shown that three-stranded units made using two interstrand Cys-Cys disulfide bridges to connect three CMP strands can self-assemble into larger fibrillar structures. However, such constructs are difficult to synthesize, because the presence of multiple disulfide bridges necessitates successive differential deprotection and coupling steps. Synthesis of two-stranded assembling units would be simpler and avoid such complications. However, two-stranded units cannot form triple-helical structure prior to assembly. Therefore, a linker with high E$_{strain}$ (e.g. Cys-Cys) would cause bigger distortions to the peptide structure and make it less collagen-like when applied to a free two-stranded assembling unit rather than a free three-stranded unit with an already-formed triple-helical core. Thus, assembly kinetics and stability of two-stranded units will be more sensitive to a linker with high E$_{strain}$.

Figure 13A:
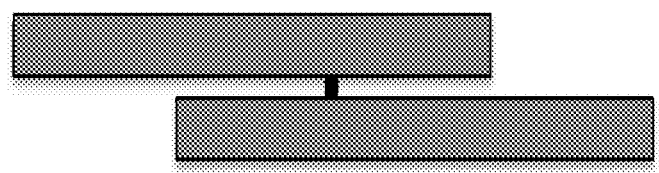
FIG. 13A is a schematic diagram of a two-stranded CMP unit containing a single optimized Hcy-Cys interstrand bridge.

Because the optimal Hcy-Cys Xaa-Yaa disulfide interstrand bridge of the present invention results in a substantially reduced E$_{strain}$, it is now possible to synthesize collagen-like fibrillar assemblies using covalently-bonded two-stranded units that do not exhibit bridge-induced disruptions to their collagen-like structure. The two-stranded units are synthesized with ease through a single coupling step forming the Hcy-Cys Xaa-Yaa disulfide interstrand bridge between the CMP strands, rather than the multiple deprotection and coupling steps required for three-stranded units. Such constructs may also feature overhanging "sticky ends" (FIG. 13A).

Figure 13B:
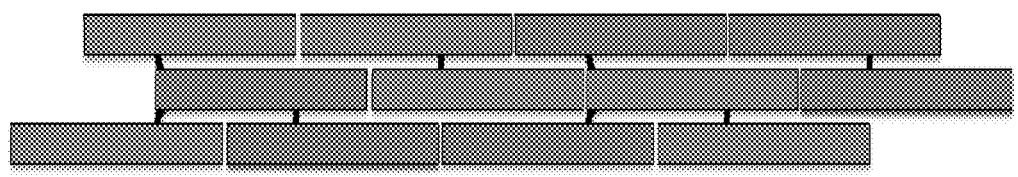
FIG. 13B is a schematic diagram showing the larger collagen-like fibrillar assemblies that can be self-assembled from such CMP units.

Each strand can be strictly designed for strand and overhang size and composition, resulting in a customized "puzzle piece" that is designed to self-assemble into a desired fibrillar assembly. A wide variety of fibrillar assemblies can be engineered using the customized "puzzle" units that include the Hcy-Cys Xaa-Yaa disulfide interstrand bridge of the present invention (FIG. 13B), and such assemblies can feature one or more "puzzle pieces."

As noted above, self-assembling systems have been designed using Cys-Cys disulfide bridges as linkers in the past. In these systems, self-assembly proceeds through the association of "sticky-ends," which predominantly relies on the recognition of a single-stranded "overhang" by a double-stranded "overhang." Because Hcy-Cys bridges do not distort the collagen backbone as much as Cys-Cys bridges, this recognition is more robust when Hcy-Cys is used instead of Cys-Cys. Furthermore, because Hcy-Cys is less destabilizing than Cys-Cys, the assembling units can be made smaller in size, both in regards to the length of peptides, and in regards to the number of strands. In addition, because Hcy-Cys bridges cause minimal disruptions to the local structure, they can be more easily applied to any site along the peptide chain.

Figure 14:
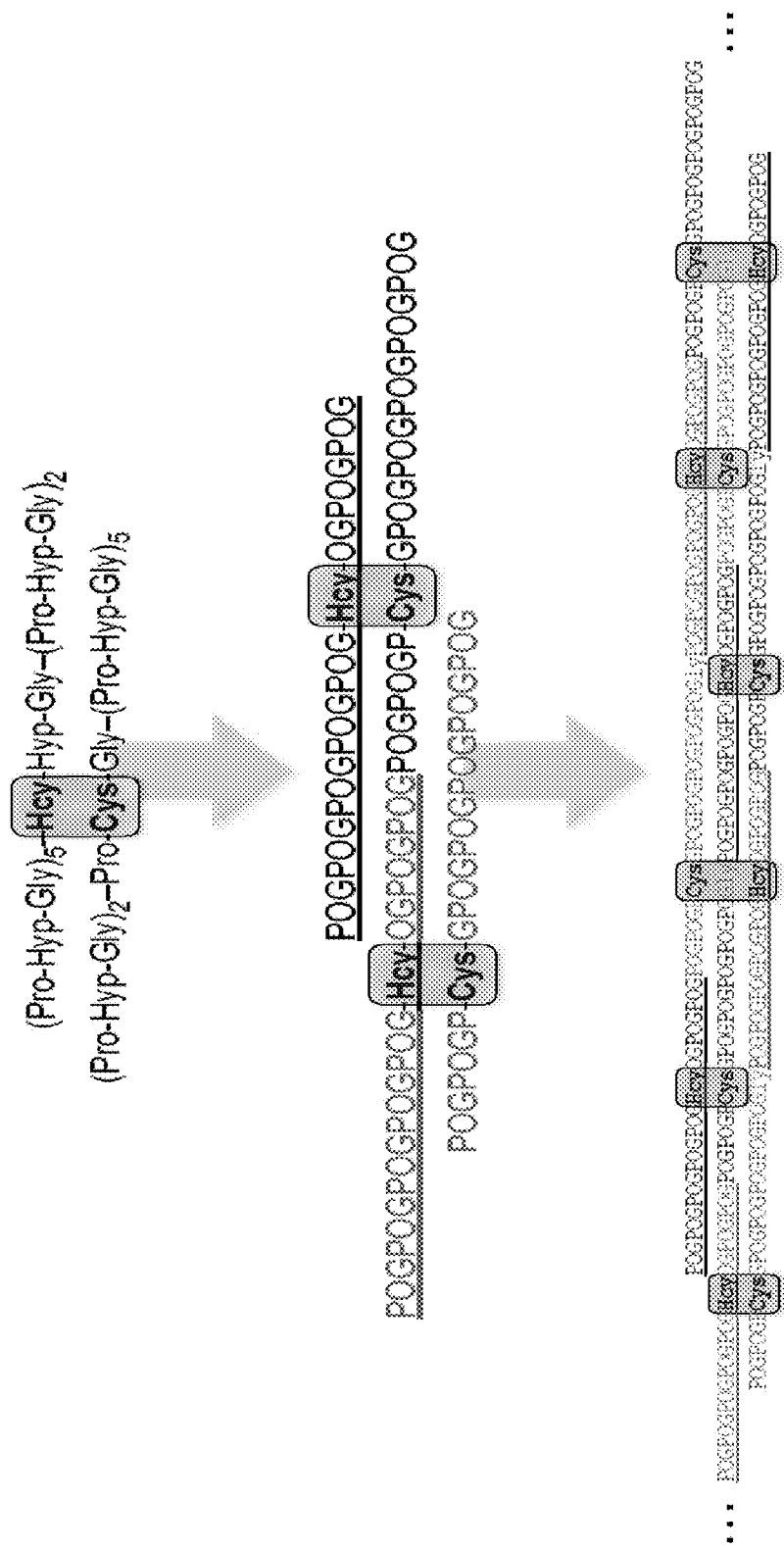
FIG. 14 shows the design of a exemplary self-assembling Hcy-Cys linked (POG)$_8$ dimer (Top Panel), and a schematic diagram showing the self-assembly of multiple such (POG)$_8$ dimers into larger structures (center and bottom panels). Amino acid sequences from top to bottom: top line is SEQ ID NO:8, second line down is SEQ ID NO:9, third line down is SEQ ID NO:10; fourth line down is SEQ ID NO:11; fifth line down is SEQ ID NO:12; sixth line down and seventh line down are both SEQ ID NO:13; and eighth line down (bottom line) is SEQ ID NO:14. "O" represents hydroxyproline.

In a non-limiting example, we have prepared a two-stranded self-assembling unit by connecting two (POG)$_8$ (SEQ ID NO:15) strands with a Hcy-Cys disulfide bridge to produce an offset that could support sticky-ended self-assembly. "O" represents hydroxyproline. This offset allows multiple 2-stranded units to associate into a triple helix that supports sticky ends for further extension (FIG. 14). Based on analytical ultracentrifugation data, this Hcy-Cys linked dimer forms assemblies that are on average 8 to 9 units long, equivalent to a [(POG)$_{45}$]$_3$ triple helix ([SEQ ID NO:16]3), when tested at 4° C. in 10 mM phosphate buffer, pH=7.

Figure 15:
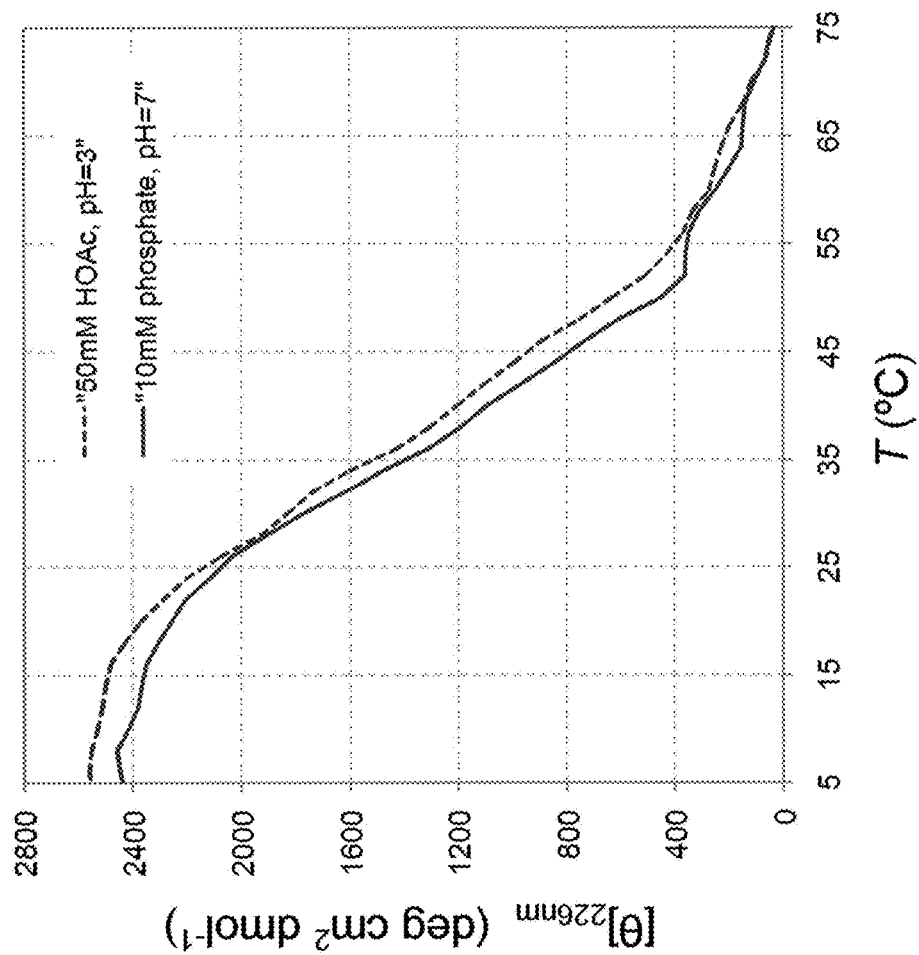
FIG. 15 is a graph showing the results of circular dichroism thermal-melt experiments of 0.1 mM (POG)$_8$-dimer (SEQ ID NO:8 and 9) in acidic and neutral conditions.

The assemblies exhibit the characteristic collagen signature peak at ~225 nm on circular dichroism spectra and produce broad melting profiles similar to those observed on a three-stranded system (Kotch, F. W.; Raines, R. T. *Proc. Natl. Acad. Sci. U.S.A.* 2006, 103, 3028-3033). The melting temperature ($T_m$) of this self-assembly system is 35° C. in 50 mM HOAc (pH ~3), surprisingly similar to the $T_m$ of [(POG)$_8$]$_3$ ((POG)$_8$ is SEQ ID NO:15) at acidic pH. Furthermore, this melting temperature does not change at neutral pH, in 10 mM phosphate buffer (FIG. 15). Shifting from acidic to neutral pH is known to decrease the thermostability of CMP trimers with charged termini, and the absence of this effect supports the sticky-ended assembly model for this system.

In sum, our results suggest that assembly through two-stranded CMP constructs is indeed possible and that the Hcy-Cys disulfide linker is compatible with this process.

Further details necessary for tuning assembly properties of this system for bio- and nano-technology applications can be determined through further experimentation.

The invention is not limited to the embodiments set forth herein for illustration, but includes everything that is within the scope of the claims. Furthermore, all references cited herein are hereby incorporated by reference in their entirety and for all purposes as if fully set forth herein.

This specification includes the sequence listing that is concurrently filed in computer readable form. This sequence listing is incorporated by reference herein.

We claim:

1. A multistranded collagen-mimetic peptide comprising a first strand consisting of the formula (Xaa-Yaa-Gly)$_n$-Hcy-Yaa-Gly-(Xaa-Yaa-Gly)$_m$, wherein Gly is glycine, Hcy is homocysteine, each Xaa is independently selected from the group consisting of proline, hydroxyproline, and lysine, and each Yaa is independently selected from the group consisting of proline, hydroxyproline, and lysine, and (i) n is zero or 1-16 and m is a positive integer from 1-16, or (ii) n is a positive integer from 1-16 and m is zero or any positive integer from 1-16; and a second strand consisting of the formula (Xaa-Yaa-Gly)$_p$-Xaa-Cys-Gly-(Xaa-Yaa-Gly)$_q$, wherein Gly is glycine, Cys is cysteine, each Xaa is independently selected from the group consisting of proline, hydroxyproline, and lysine, and each Yaa is independently selected from the group consisting of proline, hydroxyproline, and lysine, and (i) p is zero or any positive integer from 1-16 and q is a positive integer from 1-16 or (ii) p is a positive integer from 1-16 and q is zero or any positive integer from 1-16;
wherein the first and second strands are covalently bonded with a disulfide bond between the sulfur atom of the thiol side chain of the homocysteine residue of the first strand and the sulfur atom of the thiol side chain of the cysteine residue of the second strand.

2. The multi-stranded collagen-mimetic peptide of claim 1, wherein each Xaa and each Yaa is independently selected from the group consisting of proline, hydroxyproline, and lysine.

3. The multistrand collagen-mimetic peptide of claim 1, wherein each Xaa is proline and each Yaa is hydroxyproline or proline.

4. The multi-stranded collagen-mimetic peptide of claim 1, wherein the sum of p+q is from 1 to 16.

5. A multi-stranded collagen-mimetic peptide comprising:
(a) a first strand consisting of the formula (Xaa-Yaa-Gly)$_n$-Hcy-Yaa-Gly-(Xaa-Yaa-Gly)$_m$, wherein Gly is glycine, Hcy is homocysteine, each Xaa is selected from the group consisting of proline, hydroxyproline, and lysine, and each Yaa is selected from the group consisting of proline, hydroxyproline, and lysine, and (i) n is zero or any positive integer from 1-16 and m is a positive integer from 1-16, or (ii) n is a positive integer from 1-16 and m is zero or any positive integer from 1-16; and
(b) a second strand consisting of formula (Xaa-Yaa-Gly)$_p$-Xaa-Cys-Gly-(Xaa-Yaa-Gly)$_q$-Hcy-Yaa-Gly-(Xaa-Yaa-Gly)$_r$ or (Xaa-Yaa-Gly)$_p$-Hcy-Yaa-Gly-(Xaa-Yaa-Gly)$_q$-Xaa-Cys-Gly-(Xaa-Yaa-Gly)$_r$, wherein Gly is glycine, Cys is cysteine, each Xaa and each Yaa is independently selected from the group consisting of proline, hydroxyproline, and lysine, and p, q and r are independently any positive integer from 1-16.

6. The multi-stranded collagen-mimetic peptide of claim 5, further comprising (c) a third strand consisting of the formula (Xaa-Yaa-Gly)$_j$-Xaa-Cys-Gly-(Xaa-Yaa-Gly)$_k$, wherein Gly is glycine, Cys is cysteine, each Xaa and each Yaa is independently selected from the group consisting of proline, hydroxyproline, and a lysine, and j and k are independently any positive integer from 1-16;
wherein the second and third strands are covalently bonded with a disulfide bond between the sulfur atom of the thiol side chain of the homocysteine residue of the second strand and the sulfur atom of the thiol side chain of the cysteine residue of the third strand.

7. The multi-stranded collagen-mimetic peptide of claim 6, wherein (n+m+1)=(p+q+r+2); (p+q+r+2)=(j+k+1); or both.

8. The multi-stranded collagen-mimetic peptide of claim 6, wherein one of the homocysteine residues is substituted with a cysteine residue, such that either the first and second or the second and third strands are covalently bonded with a Cys-Cys disulfide bond.

9. A synthetic collagen-like fibrillar assembly comprising a plurality of the multi-stranded collagen-mimetic peptides of claim 1.

10. A composition comprising the synthetic collagen-like fibrillar assembly of claim 9 and a therapeutic agent.

11. A kit comprising a plurality of the multi-stranded collagen-mimetic peptides of claim 1.

12. The kit of claim 11, further comprising a therapeutic agent.

13. A method of making a multi-stranded collagen-mimetic peptide comprising the step of forming a covalent disulfide bond between a first strand consisting of the formula (Xaa-Yaa-Gly)$_n$-Hcy-Yaa-Gly-(Xaa-Yaa-Gly)$_m$, wherein Gly is glycine, Hcy is homocysteine, each Xaa and each Yaa is independently selected from the group consisting of proline, hydroxyproline, and a lysine, (i) n is zero or any positive integer from 1-16 and m is any positive integer from 1-16 or (ii) n is a positive integer from 1-16 and m is zero or any positive integer from 1-16; and a second strand consisting of the formula (Xaa-Yaa-Gly)$_p$-Xaa-Cys-Gly-(Xaa-Yaa-Gly)$_q$, wherein Gly is glycine, Cys is cysteine, each Xaa and each Yaa is independently selected from the group consisting of proline, hydroxyproline, and a lysine, (i) p is zero or any positive integer from 1-16 and q is any positive integer from 1-16 or (ii) p is a positive integer from 1-16 and q is zero or any positive integer;
wherein the covalent disulfide bond is formed between the sulfur atom of the thiol side chain of the homocysteine residue of the first strand and the sulfur atom of the thiol side chain of the cysteine residue of the second strand.

14. The method of claim 13, wherein each Xaa is proline and each Yaa is proline or hydroxyproline.

15. A method of making a multi-stranded collagen-mimetic peptide comprising the step of forming a covalent disulfide bond between a first strand consisting of the formula (Xaa-Yaa-Gly)$_n$-Hcy-Yaa-Gly-(Xaa-Yaa-Gly)$_m$, wherein Gly is glycine, Hcy is homocysteine, each Xaa and each Yaa is independently selected from the group consisting of proline, hydroxyproline, and a lysine, (i) n is zero or any positive integer from 1-16 and m is any positive integer from 1-16 or (ii) n is a positive integer from 1-16 and m is zero or any positive integer from 1-16; and
a second strand consisting of the formula (Xaa-Yaa-Gly)$_p$-Xaa-Cys-Gly-(Xaa-Yaa-Gly)$_q$-Hcy-Yaa-Gly-(Xaa-Yaa-Gly)$_r$ or (Xaa-Yaa-Gly)$_p$-Hcy-Yaa-Gly-(Xaa-Yaa-Gly)$_q$-Xaa-Cys-Gly-(Xaa-Yaa-Gly)$_r$,
wherein Gly is glycine, Cys is cysteine, each Xaa and each Yaa is independently selected from the group consisting of proline, hydroxyproline, and a lysine, and p, q and r are independently zero or any positive integer from 1-16,
wherein the covalent disulfide bond is formed between the sulfur atom of the thiol side chain of the homocysteine residue of the first strand and the sulfur atom of the thiol side chain of the cysteine residue of the second strand.

16. The method of claim 15, further comprising the step of forming a covalent disulfide bond between the sulfur atom of the thiol side chain of the homocysteine residue of the second strand and the sulfur atom of the thiol side chain of the cysteine residue of a third strand, wherein the third strand is consists of the formula (Xaa-Yaa-Gly)$_j$-Xaa-Cys-Gly-(Xaa-Yaa-Gly)$_k$, wherein Gly is glycine, Cys is cysteine, each Xaa and each Yaa is independently selected from the group consisting of proline, hydroxyproline, and a lysine, and j and k are independently zero or any positive integer from 1-16.

17. A method of making a synthetic collagen-like fibrillar assembly, comprising the step of contacting a first multi-stranded collagen-mimetic peptide of claim 1 with one or more second multi-stranded collagen-mimetic peptides of claim 1, whereby the first and second multi-stranded collagen-mimetic peptides self-assemble into a larger synthetic collagen-like fibrillar assembly.

18. A method of facilitating wound healing, comprising the step of contacting a wound with a composition comprising the multi-stranded collagen-mimetic peptide of claim 1, thereby facilitating the healing of the wound.

19. The method of claim 18, wherein the composition further comprises a therapeutic agent.

20. The multistrand collagen mimetic peptide of claim 1, wherein the first strand is (Pro-Pro-Gly)$_5$-Hcy-Pro-Gly-(Pro-Pro-Gly)$_4$ and the second strand is (Pro-Pro-Gly)$_4$-Pro-Cys-Gly-(Pro-Pro-Gly)$_5$, wherein Pro is proline, Gly is glycine Hcy is homocysteine and Cys is cysteine.

21. The multistrand collagen mimetic peptide of claim 1, wherein the first strand is (Pro-Pro-Gly)$_4$-Hcy-Pro-Gly-(Pro-Pro-Gly)$_4$ and the second strained is (Pro-Pro-Gly)$_4$-Pro-Cys-Gly-(Pro-Pro-Gly)$_5$, wherein Pro is proline and Gly is glycine, Hcy is homocysteine and Cys is cysteine.

22. A multistrand collagen mimetic peptide of claim 1, wherein the first strand is (Pro-Hyp-Gly)$_5$-Hcy-Hyp-Gly-(Pro-Hyp-Gly)$_5$ and the second strand is (Pro-Hyp-Gly)$_2$-Pro-Cys-Gly-(Pro-Hyp-Gly)$_5$, wherein Pro is proline, Hyp, is hydroxyproine, Gly is glycine, Hcy is homocysteine and Cys is cysteine.

* * * * *